(12) United States Patent
Takahashi et al.

(10) Patent No.: US 11,443,717 B2
(45) Date of Patent: Sep. 13, 2022

(54) BIOMETRIC INFORMATION DISPLAY DEVICE, BIOMETRIC INFORMATION DISPLAY METHOD, AND COMPUTER-READABLE RECORDING MEDIUM, EXTRACTING CURRENT COMPONENTS AT POSITIONS ALONG A NEURAL PATHWAY BASED ON CURRENT INFORMATION RECONSTRUCTED BASED ON MAGNETIC FIELD MEASUREMENT DATA GENERATED BY SUBJECT

(71) Applicants: Yoichiro Takahashi, Tokyo (JP); Taishi Watanabe, Tokyo (JP); Shigenori Kawabata, Tokyo (JP)

(72) Inventors: Yoichiro Takahashi, Tokyo (JP); Taishi Watanabe, Tokyo (JP); Shigenori Kawabata, Tokyo (JP)

(73) Assignees: Ricoh Company, Ltd., Tokyo (JP); National University Corporation Tokyo Medical and Dental University, Tokyo (JP)

( * ) Notice: Subject to any disclaimer, the term of this patent is extended or adjusted under 35 U.S.C. 154(b) by 54 days.

(21) Appl. No.: 16/953,861

(22) Filed: Nov. 20, 2020

(65) Prior Publication Data
US 2021/0158780 A1 May 27, 2021

(30) Foreign Application Priority Data
Nov. 25, 2019 (JP) .............................. JP2019-212346

(51) Int. Cl.
*G09G 5/00* (2006.01)
*G09G 5/37* (2006.01)
(Continued)

(52) U.S. Cl.
CPC ............... *G09G 5/37* (2013.01); *A61B 5/055* (2013.01); *A61B 5/742* (2013.01); *A61B 6/032* (2013.01); *G09G 2380/08* (2013.01)

(58) Field of Classification Search
CPC ....... A61B 5/062; A61B 6/505; A61B 6/5211; A61B 17/1671; G06T 7/74
See application file for complete search history.

(56) References Cited

U.S. PATENT DOCUMENTS 6,351,266 B1 * 2/2002 Kobayashi ............ G06T 11/203
345/442
10,722,701 B2  7/2020 Ishibe et al.
(Continued)

FOREIGN PATENT DOCUMENTS

JP  2006-187342    7/2006
JP  2007-125236    5/2007
(Continued)

OTHER PUBLICATIONS

Satoshi Sumiya et al: "Magnetospinography visualizes electrophysiological activity in the cervical spinal cord", Scientific Reports, vol. 7, No. 1, May 19, 2017 (May 19, 2017), XP055449754, DOI: 10.1038/s41598-017-02406-8.
(Continued)

*Primary Examiner* — Weiming He
(74) *Attorney, Agent, or Firm* — IPUSA, PLLC

(57) ABSTRACT

A biometric information display device includes a display controller configured to display a morphological image indicative of a morphology of a subject, on a display, an input controller configured to receive a designation of a specified position on the morphological image, a pathway generating section configured to generate a pathway based on the specified position on the morphological image, and a current extracting section configured to extract current components at a plurality of positions along the pathway, based
(Continued)

on current information reconstructed based on magnetic field measurement data generated by the subject. The display controller displays the current components extracted along the pathway on the display.

14 Claims, 19 Drawing Sheets

(51) Int. Cl.
  *A61B 5/055* (2006.01)
  *A61B 5/00* (2006.01)
  *A61B 6/03* (2006.01)

(56) References Cited

U.S. PATENT DOCUMENTS

| | | |
|---|---|---|
| 2018/0008223 A1 | 1/2018 | Yamagata |
| 2019/0167135 A1 | 6/2019 | Okada et al. |
| 2019/0254552 A1* | 8/2019 | Melgaard ............ A61N 1/3704 |

FOREIGN PATENT DOCUMENTS

| | | |
|---|---|---|
| JP | 2008-178558 | 8/2008 |
| JP | 4791797 | 10/2011 |
| JP | 2017-099450 | 6/2017 |
| JP | 2019-098156 | 6/2019 |

OTHER PUBLICATIONS

Watanabe Taishi et al: "Novel functional imaging technique for the brachial plexus based on magnetoneurography", Clinical Neurophysiology, Elsevier Science, IE, vol. 130, No. 11, Aug. 22, 2019 (Aug. 22, 2019), pp. 2114-2123, XP085865622, ISSN: 1388-2457, DOI: 10.1016/J.CLINPH.2019.08.006 [retrieved on Aug. 22, 2019].
Sasaki T et al: "Visualization of electrophysiological activity in patients with carpal tunnel syndrome using magnetoneurography", Journal of Neurological Sciences, Elsevier Scientific Publishing Co, Amsterdam, NL, vol. 405, Oct. 15, 2019 (Oct. 15, 2019), p. 23, XP085982477, ISSN: 0022-510X, DOI: 10.1016/J.JNS.2019.10.1589.
Extended European Search Report for EP20208418.2 dated Apr. 20, 2021.

* cited by examiner

FIG.5
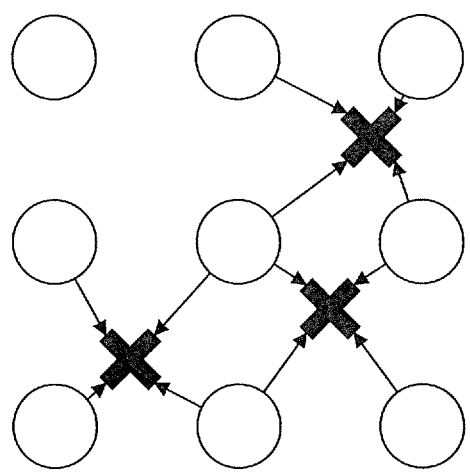
 : POSITION OF VIRTUAL ELECTRODE
 : RECONSTRUCTED VOXEL

BIOMETRIC INFORMATION DISPLAY DEVICE, BIOMETRIC INFORMATION DISPLAY METHOD, AND COMPUTER-READABLE RECORDING MEDIUM, EXTRACTING CURRENT COMPONENTS AT POSITIONS ALONG A NEURAL PATHWAY BASED ON CURRENT INFORMATION RECONSTRUCTED BASED ON MAGNETIC FIELD MEASUREMENT DATA GENERATED BY SUBJECT

CROSS REFERENCE TO RELATED APPLICATIONS

The present application is based upon and claims priority to Japanese Patent Application No. 2019-212346, filed on Nov. 25, 2019, the entire contents of which are incorporated herein by reference.

BACKGROUND OF THE INVENTION

1. Field of the Invention

The present disclosure relates to a biometric information display device, a biometric information display method, and a computer-readable recording medium.

2. Description of the Related Art

In a magnetic field measuring device for measuring a magnetic field generated by a living body, a technique that estimates a current flowing through the living body based on the measured magnetic field, and displays the estimated current distribution, waveform, isocontour field distribution of the magnetic field, or the like in multiple windows of a single screen, is described in Japanese Unexamined Patent Application Publication No. 2008-178558, for example.

In addition, in a magnetocardiograph, a technique that obtains an intramyocardial current distribution as an appropriate current value based on the measured magnetic field data, and displays the current distribution on a display device, is described in Japanese Unexamined Patent Application Publication No. 2007-125236, for example.

The current generated by a nerve activity includes an intra-axonal current component that flows through the nerve axon, and a volume current component that flows outside the nerve axon and returns back to a depolarization point. For example, the intra-axonal current component and the volume current component, estimated from the magnetic field data measured by the magnetic field measuring device, may be superimposed on a morphological image of a part of the living body to be measured. The superimposed image may be displayed on the display device, and a nerve function may be evaluated based on the displayed information.

Because the intra-axonal current component flows along a neural pathway, positions where the intra-axonal current component is to be extracted are required to be set according to the actual neural pathway, in order to extract the correct intra-axonal current component from the magnetic field data. For example, in a case where the neural pathway is curved, the positions where the intra-axonal current component is to be extracted are required to be set according to the curved shape of the neural pathway.

The correct intra-axonal current component cannot be obtained, and the nerve function cannot be correctly evaluated, if the positions where the intra-axonal current component is to be extracted are not set along the curved shape of the actual neural pathway. Similar to the intra-axonal current component, positions where the volume current component is to be extracted are required to be set according to the curved shape of the neural pathway, in order to estimate the correct volume current component.

SUMMARY

According to one aspect of the embodiments, a biometric information display device includes a display controller configured to display a morphological image indicative of a morphology of a subject, on a display; an input controller configured to receive a designation of a specified position on the morphological image; a pathway generating section configured to generate a pathway based on the specified position on the morphological image; and a current extracting section configured to extract current components at a plurality of positions along the pathway, based on current information reconstructed based on magnetic field measurement data generated by the subject, wherein the display controller displays the current components extracted along the pathway on the display.

Other features of the embodiments will be apparent from the following detailed description when read in conjunction with the accompanying drawings.

BRIEF DESCRIPTION OF THE DRAWINGS

FIG. 5 is a diagram for explaining an example of a method for calculating a current intensity at the virtual electrode.

DESCRIPTION OF THE EMBODIMENTS

Figure 1:
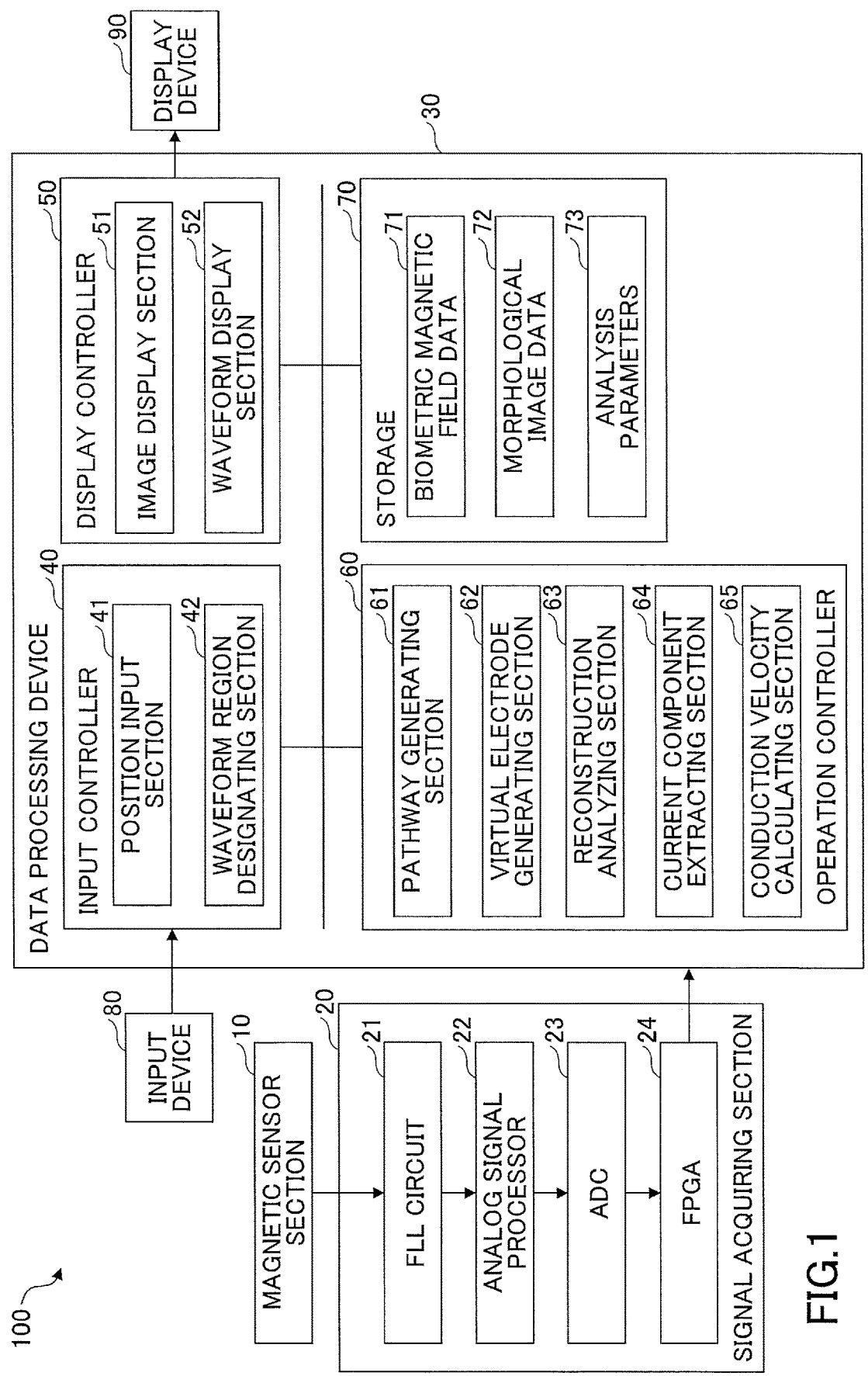
FIG. 1 is a block diagram illustrating an example of a biometric information measuring apparatus including a biometric information display device according to one embodiment of the present invention.

Embodiments will hereinafter be described with reference to the drawings. In drawings, the same constituent elements are designated by the same reference numerals, and a repeated description of the same constituent elements may be omitted.

One object of the embodiments is to provide a biometric information display device, a biometric information display method, and a computer-readable recording medium, which can generate a pathway from which a current component is to be extracted from a subject (or test subject), using a morphological image of the subject.

FIG. 1 is a block diagram illustrating an example of a biometric information measuring apparatus including a biometric information display device according to one embodiment of the present invention. For example, a biometric information measuring apparatus 100 illustrated in FIG. 1 includes a magnetic sensor section 10, a signal acquiring section 20, a data processing device 30, an input device 80, and a display device 90. The data processing device 30 may be a computer, such as a personal computer (PC), a server, or the like, that functions as the biometric information display device. The display device 90 is capable of displaying a morphological image of a subject, such as an X-ray image or the like. The morphological image of the subject is indicative of a morphology of the subject. The display device 90 is an example of a display or display means. The display device 90 may be included in the biometric information display device, or may be externally connected to the biometric information display device, as appropriate.

The signal acquiring section 20 includes a flux locked loop (FLL) circuit 21, an analog signal processor 22, an analog-to-digital converter (ADC) 23, and a field programmable gate array (FPGA) 24. For example, the magnetic sensor section 10 and the signal acquiring section 20 are provided inside a shielded enclosure that provides magnetic shielding, while the data processing device 30, the input device 80, and the display device 90 are provided outside the shielded enclosure. For example, the magnetic sensor section 10 includes a plurality of superconducting quantum interference device (SQUID) magnetic sensors. The magnetic sensor section 10 may include other types of magnetic sensors, such as magneto resistive (MR) sensors, optically pumped atomic magnetometer (OPAM) sensors, or the like, in place of the SQUID magnetic sensors.

The data processing device 30 includes an input controller 40, a display controller 50, an operation controller 60, and a storage 70. For example, functions of the input controller 40, the display controller 50, and the operation controller 60 may be performed by a processor, such as a central processing unit (CPU) or the like provided in the data processing device 30, that implements a biometric information display method by executing a display program while cooperating with hardware. The input controller 40 is an example of an input control circuit or means, and the display controller 50 is an example of a display control circuit or means.

The biometric information measuring apparatus 100 may be used as a magnetoencephalograph (MEG), a magnetocardiograph (MCG), a magnetospinograph (MSG), or the like. The biometric information measuring apparatus 100 may be applied to measurements of a neural magnetic field, a muscular magnetic field, or the like, other than a spinal magnetic field.

The magnetic sensor section 10 measures the magnetic field generated by the subject, and outputs the measured magnetic field as a voltage. The magnetic sensor 10 includes the plurality of SQUID magnetic sensors that are provided at positions opposing magnetic field measuring parts of the subject lying on a bed, for example. The FLL circuit 21 improves a dynamic range of the magnetic sensor section 10 by linearizing each of nonlinear magnetic field-voltage characteristics measured by the plurality of SQUID magnetic sensors.

The analog signal processor 22 amplifies the linearized analog signal output from the FLL circuit 21, and performs a filter processing or the like on the amplified analog signal. The ADC 23 converts the filtered analog signal (magnetic field signal) into a digital value (magnetic field data). The FPGA 24 further performs a filtering process, a thinning process, or the like on the digitized magnetic field data from the ADC 23, and transmits the processed data to the data processing device 30.

In the data processing device 30, the input controller 40 includes a position input section 41 and a waveform region designating section 42, and performs an input process on various information input by an operator of the data processing device 30 via the input device 80, such as a mouse, a keyboard, or the like. Functions of the position input section 41 and the waveform region designating section 42 will be described later.

The display controller 50 includes an image display section 51 and a waveform display section 52, and performs a control to display the X-ray image, a current waveform, or the like on the display device 90, such as a liquid crystal display (LCD) or the like. Functions of the image display section 51 and the waveform display section 52 will be described later. The input device 80 and the display device 90 may be included in the data processing device 30. In addition, an output device, such as a printer or the like, may be connected to the data processing device 30.

The operation controller 60 includes a pathway generating section 61, a virtual electrode generating section 62, a reconstruction analyzing section 63, a current component extracting section 64, and a conduction velocity calculating section 65. The pathway generating section 61 is an example of a pathway generating circuit or means, the virtual electrode generating section 62 is an example of a virtual electrode generating circuit or means, and the current component extracting section 64 is an example of a current component extracting circuit or means. The conduction velocity calculating section 65 is an example of a conduction velocity calculating circuit or means. Functions of the pathway generating section 61, the virtual electrode generating section 62, the reconstruction analyzing section 63, the current component extracting section 64, and the conduction velocity calculating section 65 will be described later.

The storage 70 may be formed by a storage device, such as a hard disk drive (HDD) or the like, and includes an area for storing biometric magnetic field data 71, morphological image data 72, and various analysis parameters 73. The biometric magnetic field data 71 include measurement data of the magnetic field measured by the magnetic sensor section 10 and processed by the signal acquiring section 20. The morphological image data 72 include X-ray image data captured by an X-ray machine, magnetic resonance (MR) image data captured by a magnetic resonance tomographic machine, or the like. In the following description, an X-ray morphological image of the subject generated from the X-ray image data will be referred to as the X-ray image, and a morphological image of the subject generated from the MR image data will be referred to as the MR image. In addition, a morphological image of the subject generated from the computed tomography (CT) scan image data will be referred to as a CT image.

The analysis parameters 73 include setting values of a filter (highpass filter, lowpass filter, or the like) provided in the signal acquiring section 20, parameters required for measuring the biometric magnetic field, such as a time range, a number of elements, or the like for performing various signal processing, and parameters required for implementing the biometric information display method.

Figure 2:
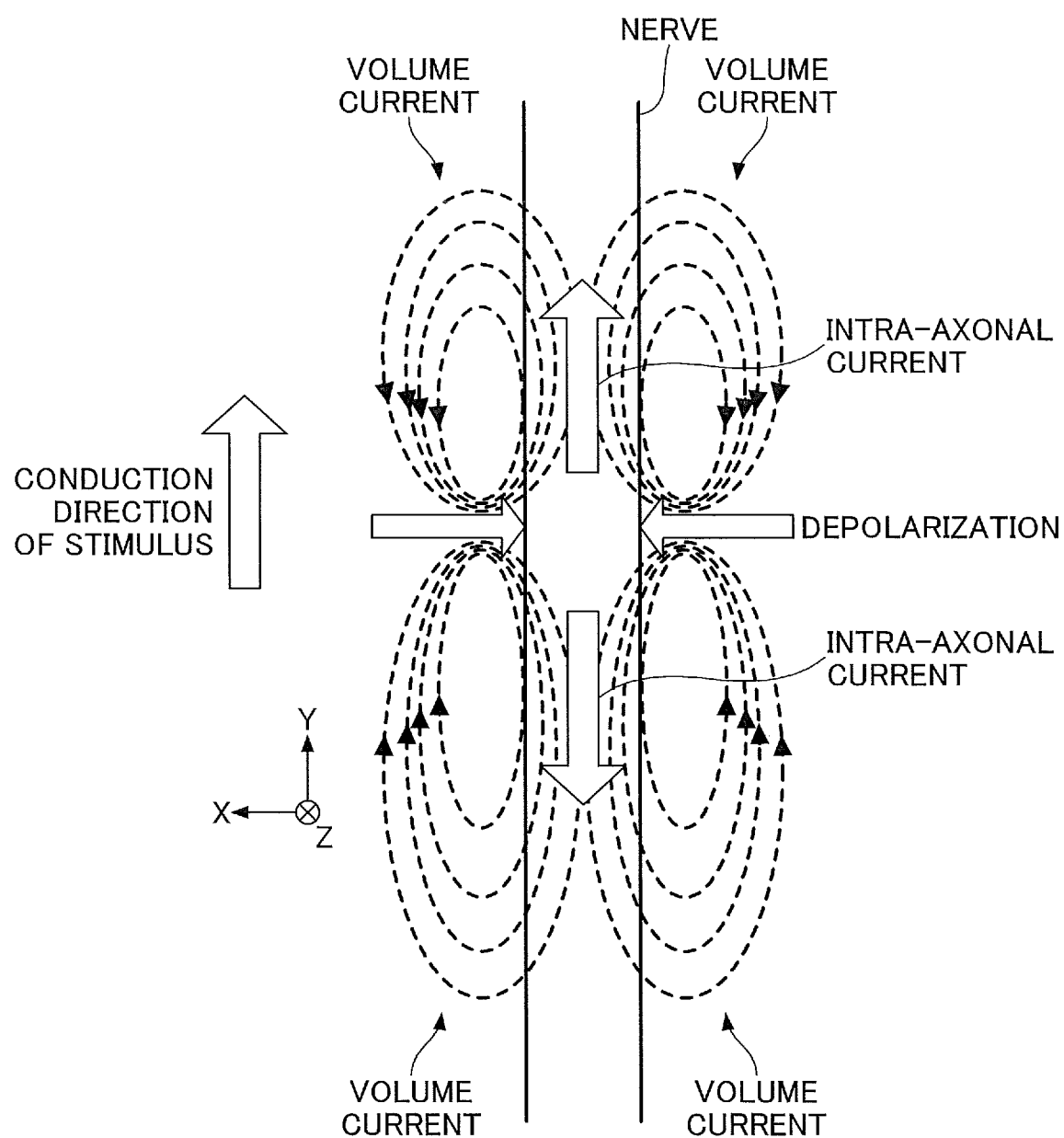
FIG. 2 is a diagram for explaining an example of a model of a nerve activity current.

FIG. 2 is a diagram for explaining an example of a model of a nerve activity current. FIG. 2 illustrates a manner in which a current is generated by an activity of a nerve running linearly in an up-and-down (or vertical) direction in FIG. 2, where a lower end in FIG. 2 corresponds to the side closer to a peripheral nerve, and an upper end in FIG. 2 corresponds to the side closer to a central nerve. For example, by applying an electrical stimulation to the peripheral nerve, the electrical stimulation is transferred, as the current, from the lower end toward the upper end of the nerve axon.

In this state, an intra-axonal current and a volume current are generated. The intra-axonal current includes an intra-axonal current component that flows toward the upper end (in a forward direction) in FIG. 2, and an intra-axonal current component that flows toward the lower end (in a reverse direction) in FIG. 2. The volume current includes a volume current component that flows outside the nerve axon and returns back to a depolarization point. In the following description, the intra-axonal current component that flows toward the upper end in FIG. 2 will be referred to as a leading component, and the intra-axonal current component that flows toward the lower end in FIG. 2 will be referred to as a trailing component.

In order to evaluate the nerve function in detail, the intra-axonal current flowing along the nerve axon, and a current flowing perpendicularly into the nerve axon due to the volume current, can be extracted and visually displayed on a screen or the like of the display device 90.

Figure 3:
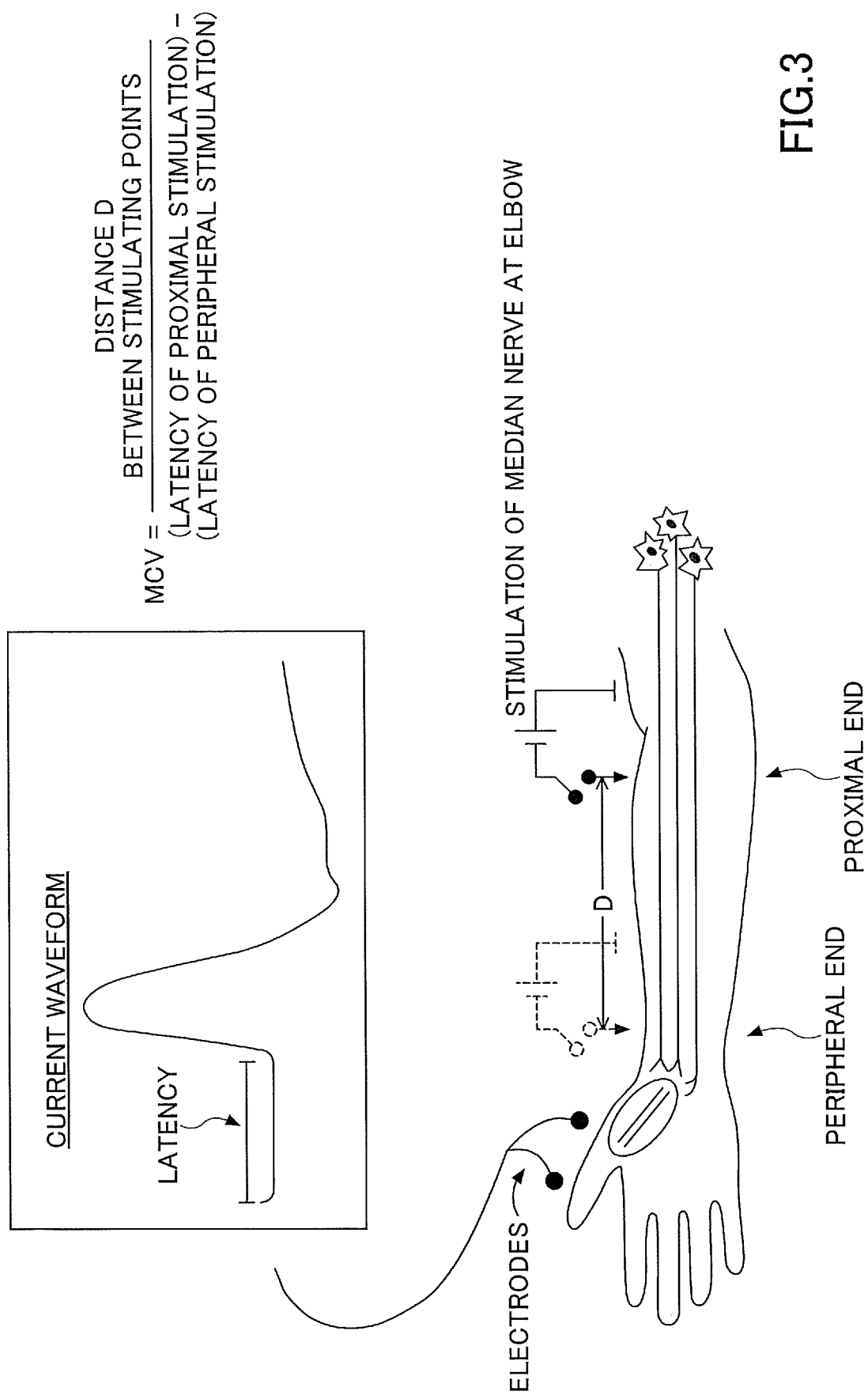
FIG. 3 is a diagram for explaining an example of a method for calculating a motor nerve conduction velocity.

FIG. 3 is a diagram for explaining an example of a method for calculating a motor nerve conduction velocity. In FIG. 3, the electrical stimulation is applied to each of a proximal end of a median nerve (for example, near an elbow) and a peripheral end (for example, near a wrist), currents generated in response to the electrical stimulation are measured by an electromyograph or the like via an electrode attached to a palm, and latencies of the currents are calculated from the measured current waveforms (time variations of current intensity). By dividing a distance between the stimulating points by a latency difference, a motor nerve conduction velocity (MCV), that is a conduction velocity of the stimulus inside the subject, can be obtained. As will be described later, by reconstructing (extracting) the current components from the magnetic field data, it is possible to calculate the MCV using the reconstructed current components, without having to measure the currents using the electromyograph or the like.

Figure 4:
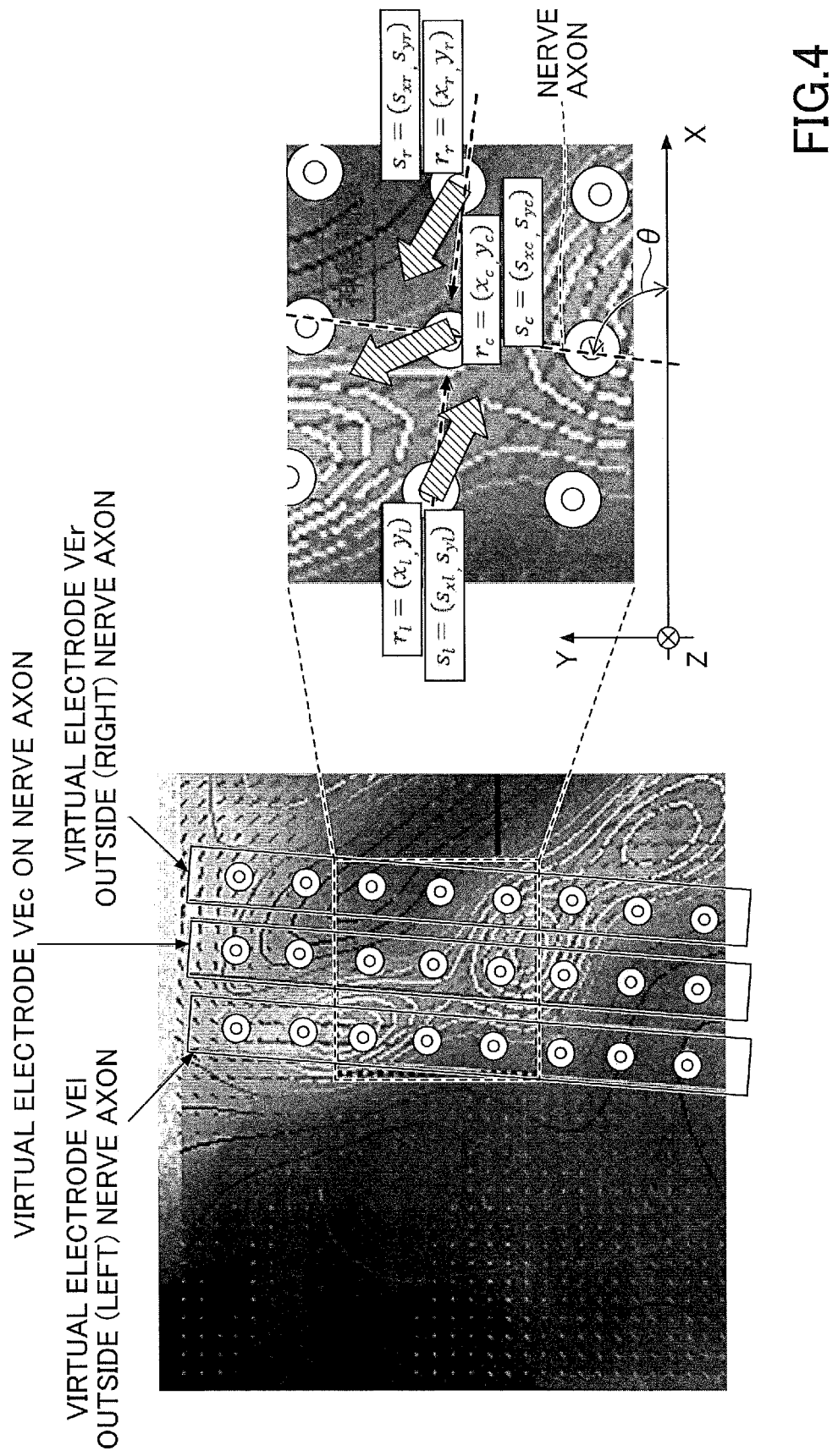
FIG. 4 is a diagram for explaining an example in which virtual electrodes are set by a data processing apparatus illustrated in FIG. 1.

FIG. 4 is a diagram for explaining an example in which virtual electrodes VE (VEc, VEl, and VEr) are set by the data processing device 30 illustrated in FIG. 1. In the following description, when describing the virtual electrodes VEc, VEl, and VEr without distinguishing these virtual electrodes from one another, these virtual electrodes may also be referred to as virtual electrodes VE. The virtual electrode VEc is an example of a first virtual electrode, the virtual electrode VEl is an example of a second virtual electrode, and the virtual electrode VEr is an example of a third virtual electrode.

Here, the virtual electrode VE refers to an imaginary electrode that is virtually set on the X-ray image or the MR image of the subject, and indicates a current extraction point (current observation point) at which the current component is to be extracted (reconstructed) from magnetic field data, among the magnetic field measuring parts of the subject. Since the method for extracting the current is known, a detailed description thereof will be omitted.

In FIG. 4, an X-Y plane is parallel to a sensing surface of an SQUID magnetic sensor array, an X direction is the direction in which the SQUID magnetic sensor array is arranged, a Y direction is perpendicular to the X direction, and a Z direction is perpendicular to the X-Y plane and toward the SQUID magnetic sensor array. Symbols $r_c$, $s_c$, $r_l$, $s_l$, $r_r$, and $s_r$ illustrated in FIG. 4 denote the following contents.

$r_c$: Intra-axonal current acquiring position=$(x_c, y_c)$
$s_c$: Estimated current=$(s_{xc}, s_{yc})$ at $r_c$
$r_l$: Left volume current acquiring position=$(x_l, y_l)$
$s_l$: Estimated current=$(s_{xl}, s_{yl})$ at $r_l$
$r_r$: Right volume current acquiring position=$(x_r, y_r)$
$s_r$: Estimated current=$(s_{xr}, s_{yr})$ at $r_r$
θ: Angle of the nerve axon (=angle of nerve axon direction with respect to X direction)

In FIG. 4, a plurality of virtual electrodes VEc are set on a neural pathway (nerve axon) running linearly in the morphological image (X-ray image) of the subject. In addition, virtual electrodes VEl and VEr outside (left and right sides of) the nerve axon are set on both sides of the nerve axon (in a direction perpendicular to the neural pathway) at each virtual electrode VEc. In FIG. 4, rectangles illustrated in peripheries of the virtual electrodes VEc, VEl, and VEr indicate definitions of the symbols $r_c$, $s_c$, $r_l$, $s_l$, $r_r$, and $s_r$ for facilitating the reader's understanding, and these rectangles are not displayed on the actual screen.

In FIG. 4, a plurality of small arrows superimposed on the morphological image indicate directions of the currents extracted by reconstruction, and the length of each arrow indicates a current intensity. In the arrow, an end opposite the arrowhead indicates the position of a voxel that is the extraction unit of the current component. Further, a contour-like curve indicates a current intensity distribution that is generated by connecting the positions where the current intensities are the same. The arrows and the current intensity distribution indicating the current components are also illustrated in the morphological images illustrated in FIG. 7 and FIG. 17 which will be described later.

The neural pathway passing through the nerve axon is generated by the pathway generating section 61, by detecting, by the position input section 41, a plurality of positions designated on the morphological image via the input device 80, and making calculations in the pathway generating section 61 using coordinates of the plurality of detected positions. For example, the positions indicating the neural pathway of the nerve axon may be input from the input device 80 by the operator who operates the data processing device 30 while viewing the nerve in the morphological image.

Alternatively, the neural pathway of the nerve axon may be set by the data processing device 30 which infers (or derives) the position, running (or extending) direction, or the like of the nerve in the morphological image. In the case where the neural pathway of the nerve axon is set by inference, a machine learning, such as deep learning or the like, may be performed using a large number of morphological images in which the neural pathway is known in advance, and a neural network for setting the neural pathway may be constructed in the data processing device 30 as the pathway generating section 61. The neural network for setting the neural pathway may be constructed in a cloud (or cloud computing system) that is connected to the data processing device 30 via a network, and may be used by the data processing device 30.

The pathway generating section 61 notifies information indicating the calculated neural pathway to the virtual electrode generating section 62. The calculated neural pathway may be represented by a formula or the like indicating a plurality of coordinate information or a curve. The virtual electrode generating section 62 generates a plurality of virtual electrodes VEc at equal spacing, for example, on the neural pathway notified from the pathway generating section 61. The spacing and the number of virtual electrodes VEc generated on the neural pathway, are specified by the operator via the input device 80, and stored in the storage 70 by the input controller 40. The virtual electrode generating section 62 generates the virtual electrodes VEc on the neural pathway generated by the pathway generating section 61, according to the spacing and the number of virtual electrodes VEc stored in the storage 70.

The virtual electrode generating section 62 sets the virtual electrode VEl and the virtual electrode VEr outside the nerve axon, on both sides of the virtual electrode VEc, that is, on the left side and the right side of the virtual electrode VEc, respectively. A distance from the virtual electrode VEc to the virtual electrodes VEl and VEr outside the nerve axon, may be specified by the operator via the input device 80, similar to the spacing between the virtual electrodes VEc. In a case where the storage 70 does not store information indicating at least one of the spacing, the number, and the distance of the virtual electrodes VE, the virtual electrode generating section 62 may generate the virtual electrodes VE using preset default values.

The image display section 51 displays the morphological image on the screen of the display device 90, and displays the virtual electrodes VEc, VEl, and VEr generated by the virtual electrode generating section 62 in a state superimposed on the morphological image, as illustrated in FIG. 4. When the virtual electrode generating section 62 generates the virtual electrodes VEc, VEl, and VEr, the arrows indicating the currents and the current intensity distribution may be superimposed on the morphological image and displayed on the screen of the display device 90, or only the morphological image may be displayed on the screen of the display device 90, as appropriate.

The reconstruction analyzing section 63 operates independently of the above described operations of the pathway generating section 61 and the virtual electrode generating section 62, and reconstructs the current component for each of the voxels that are virtual current extraction points arranged at a predetermined spacing, using the magnetic field data of the subject measured by the magnetic sensor section 10. As illustrated in FIG. 4, the image display section 51 superimposes the arrow representing the direction and intensity of the current indicated by the reconstructed current component, on the morphological image and the virtual electrodes VEc, VEl, and VEr, to be displayed on the screen of the display device 90.

The current component extracting section 64 extracts the current component (current density distribution) at each virtual electrode VE using the current component at each voxel, based on a positional relationship between the voxels and each of the virtual electrode VEc, VEl, and VEr. An example of the extraction of the current component will be described with reference to FIG. 5.

For example, the current component extracting section 64 calculates the waveform for the intra-axonal current that conducts through the nerve axon, from the current component along the nerve axon, by regarding the head side of the arrow as being positive and the tail side of the arrow as being negative. The current component extracting section 64 calculates the waveform of the volume current, from the component perpendicular to the nerve axon, by regarding the direction toward the nerve axon as being positive. The component of the volume current, perpendicular to the nerve axon, can be used to evaluate the nerve function.

For example, the estimated current of each virtual electrode VE can be calculated from the following formulas (1), (2), and (3), where $/S_c$ denotes the intra-axonal current from the virtual electrode VEc when the virtual electrode VEc is regarded as a base point, $/S_l$ denotes the left volume current from the virtual electrode VEl when the virtual electrode VEl is regarded as a base point, $/S_r$ denotes the right volume current from the virtual electrode VEr when the virtual electrode VEr is regarded as a base point, and a symbol "/" indicates an overbar.

$$\bar{s}_c = s_{xc} \cos\theta + s_{yc} \sin\theta \quad (1)$$

$$\bar{s}_l = s_{xl} \sin\theta - s_{yl} \cos\theta \quad (2)$$

$$\bar{s}_r = -s_{xr} \sin\theta + s_{yr} \cos\theta \quad (3)$$

By calculating the formulas (1) through (3) with respect to the estimated current at all of the measured points in time, it is possible to acquire the current waveforms in which the values vary with the lapse of time.

FIG. 5 is a diagram illustrating an example of a method of calculating the current intensity at the virtual electrode VE. In FIG. 5, the current intensity at the virtual electrode VE is calculated from the intensity of the current reconstructed on the voxels that are arranged in a matrix arrangement, using a linear interpolation technique. By this operation, it is possible to calculate the estimated intensity of the current in the X direction and the Y direction in FIG. 4, at the virtual electrode VE.

In FIG. 5, the spacing of the voxels and the spacing of the virtual electrodes VE are approximately the same for the sake of convenience, to facilitate the reader's understanding thereof. However, in actual practice, the spacing of the virtual electrodes VE is several times the spacing of the voxels as illustrated in FIG. 4, for example, and the spacing of the voxels and the spacing of the virtual electrodes VE may be set arbitrarily. In addition, with respect to the SQUID magnetic sensors that are arranged at a spacing that is several centimeters (cm), the voxels are arranged at the spacing of several millimeters (mm).

The current intensity at the virtual electrode VE may be calculated using the recursive null steering (RENS) filter method studied by the present inventors. In this case, the current intensity at each virtual electrode VE can be calculated accurately in a short period of time, compared to the case where the current intensity is calculated by the linear interpolation technique.

Figure 6:
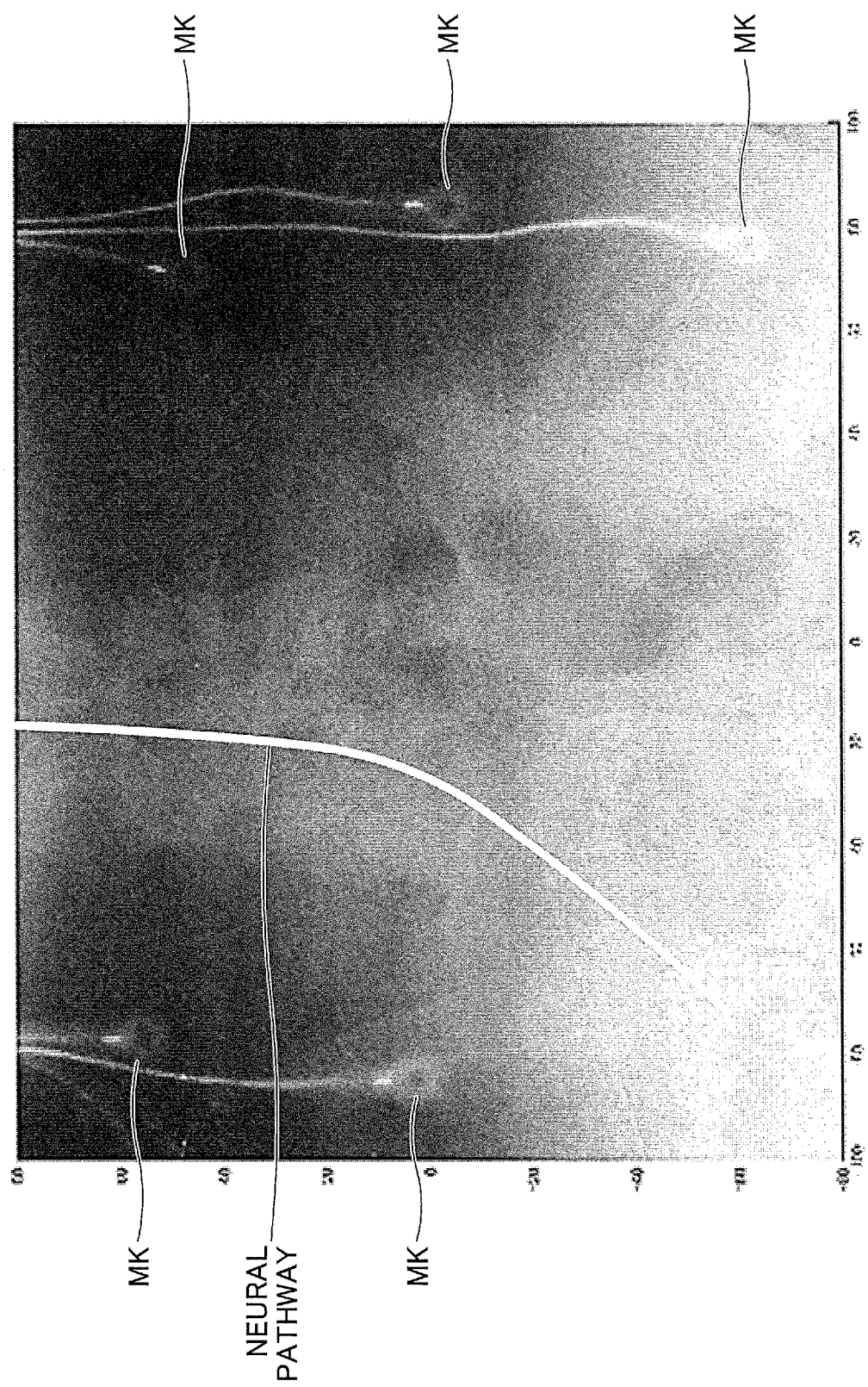
FIG. 6 is a diagram for explaining a neural pathway running from a right foot to a lumbar part.

FIG. 6 is a diagram for explaining a neural pathway running from a right foot to a lumbar part. FIG. 6 illustrates the X-ray image of the subject displayed on the display device 90. As represented by a thick white line in FIG. 6, the neural pathway from a sciatic nerve to a spinal cord, for example, when viewed from the front of the subject, has a curved shape and not a linear shape. In this embodiment, the pathway generating section 61 can set the neural pathway as a curve.

By setting the neural pathway as the curve, measurements similar to those of spinal cord evoked potential measurement methods can be made from a body surface non-invasively using the virtual electrodes VE, and it is possible to evaluate the nerve function in detail without imposing strain on the subject. The spinal cord evoked potential measurement methods perform the measurements by inserting an electrode into a spinal canal, and measuring a potential of the spinal cord at an immediate vicinity of the spinal cord.

A marker MK illustrated in FIG. 6 corresponds to an electrode that is captured together with the subject to align and coordinate the morphological image, such as the X-ray image or the like, with the measuring position where the magnetic field data are measured by the SQUID magnetic sensors, and this electrode is mounted at a position opposing (or facing) the body surface of the subject. A predetermined current is applied to the marker MK, in order to identify the position of the marker MK by the SQUID magnetic sensors.

Figure 7:
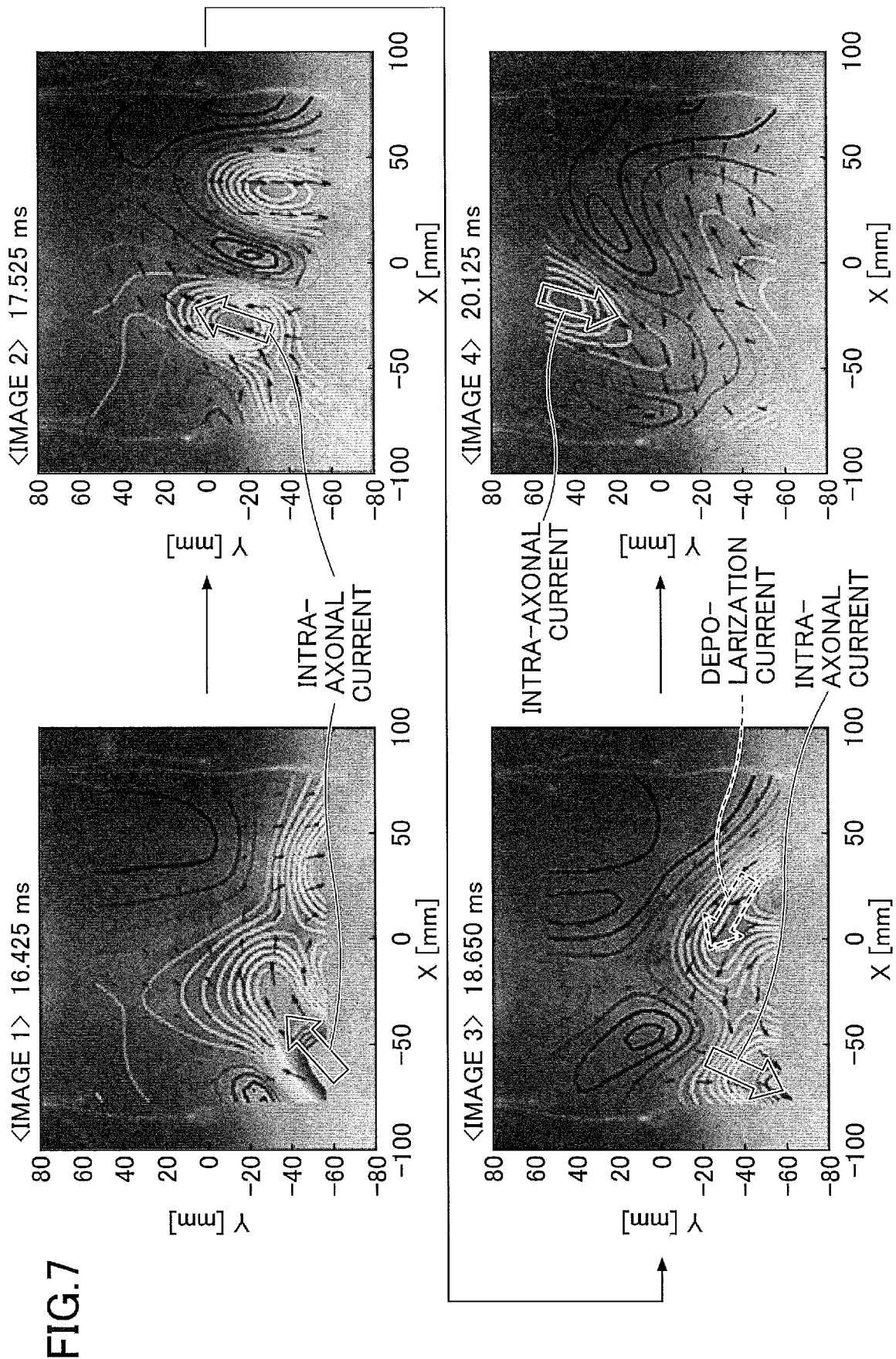
FIG. 7 is a diagram for explaining an example of the nerve activity current generated along the neural pathway illustrated in FIG. 6.

FIG. 7 is a diagram for explaining an example of the nerve activity current generated along the neural pathway illustrated in FIG. 6. FIG. 7 illustrates a time variation of the current distribution at parts of the subject to be measured. Images illustrated in FIG. 7 are displayed on the screen of the display device 90 by the image display section 51, based on current data, that is, current information of each of the voxels reconstructed by the reconstruction analyzing section 63. These images, displayed on the screen of the display device 90, are superimposed on the X-ray image.

FIG. 7 illustrates four images 1 through 4 in which the current state varies with the lapse of time. The four images 1 through 4 may be displayed simultaneously on the screen, or one of the four images 1 through 4 may be displayed at one time. In the latter case, a slide bar or the like indicating the time and displayed on the screen, may be manipulated by the operator to successively switch the image that is displayed in a single window on the screen. Bold solid arrows representing the intra-axonal current, and bold dotted arrows representing the volume current, are additionally illustrated in FIG. 7 for facilitating the reader's understanding, and these bold solid arrows and bold dotted arrows are not included in the image displayed on the screen.

In the image 1 (latency=16.425 ms), the presence of the leading component of the current toward the spinal canal can be observed. In the image 2 (latency=17.525 ms), a state of the leading component of the current conducting toward the head side can be confirmed. In the image 3 (latency=18.650 ms) and the image 4 (latency=20.125 ms), the trailing components behaving in the same manner as the leading component can be observed. In addition, in the image 3, a component of a depolarization current toward the nerve axon can be observed together with the trailing component.

Figure 17:
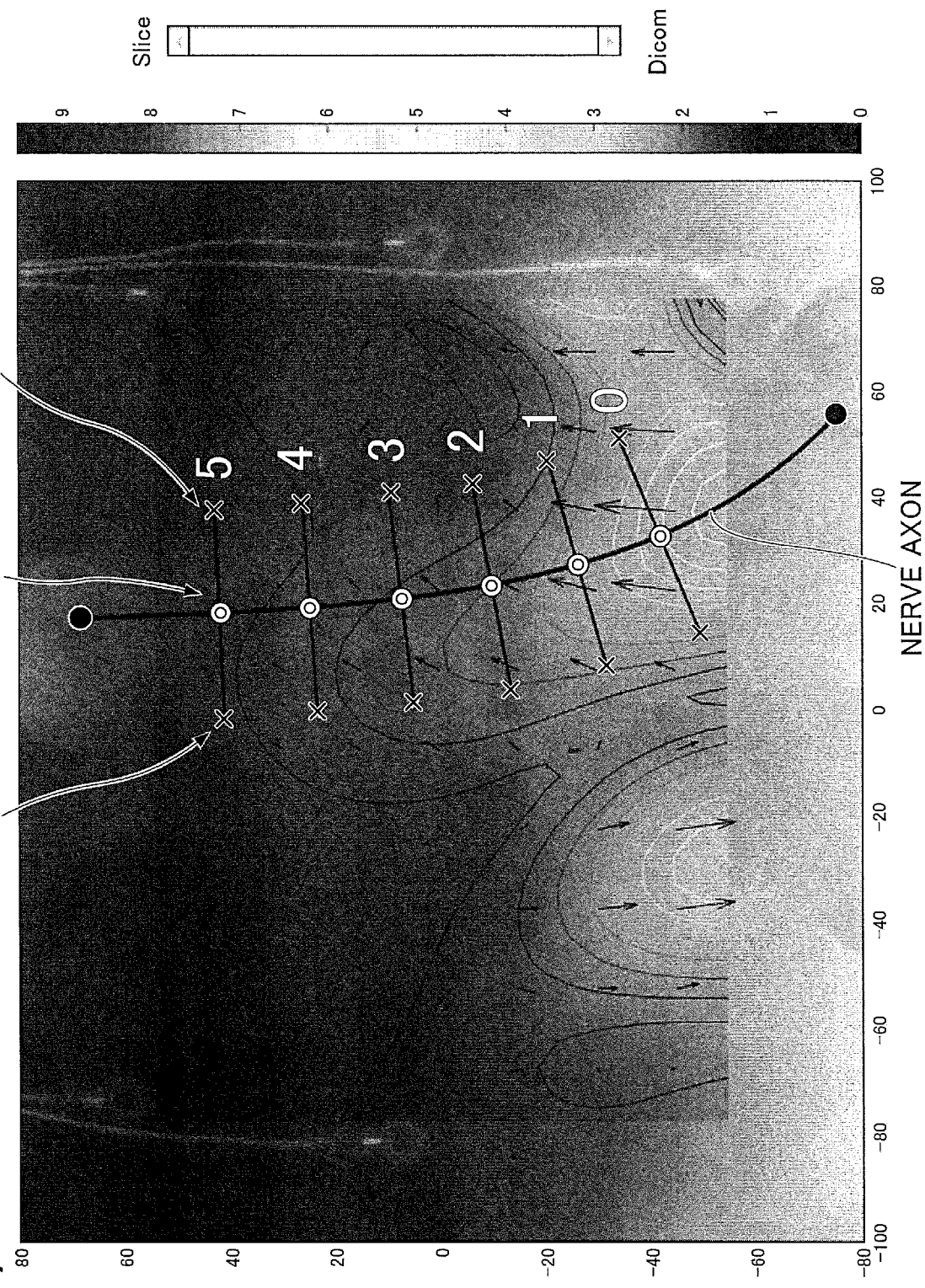
FIG. 17 is a diagram for explaining an example in which the virtual electrodes are set along the neural pathway running from a left foot to the lumbar part.

From the four images 1 through 4 illustrated in FIG. 7, it may be seen that the intra-axonal current flows through the neural pathway illustrated in FIG. 6. Accordingly, by setting the virtual electrodes VEc, VEl, and VEr along the neural pathway illustrated in FIG. 6, it is possible to extract the intra-axonal current and the depolarization current (volume current) represented by the arrows in FIG. 7, by the technique illustrated in FIG. 5. As illustrated in FIG. 17 which will be described later, the neural pathway, the virtual electrodes VEc, VEl, VEr, or the like may further be superimposed on the image in which the arrows representing the currents and the current intensity distribution are superimposed on the morphological image.

Figure 8:
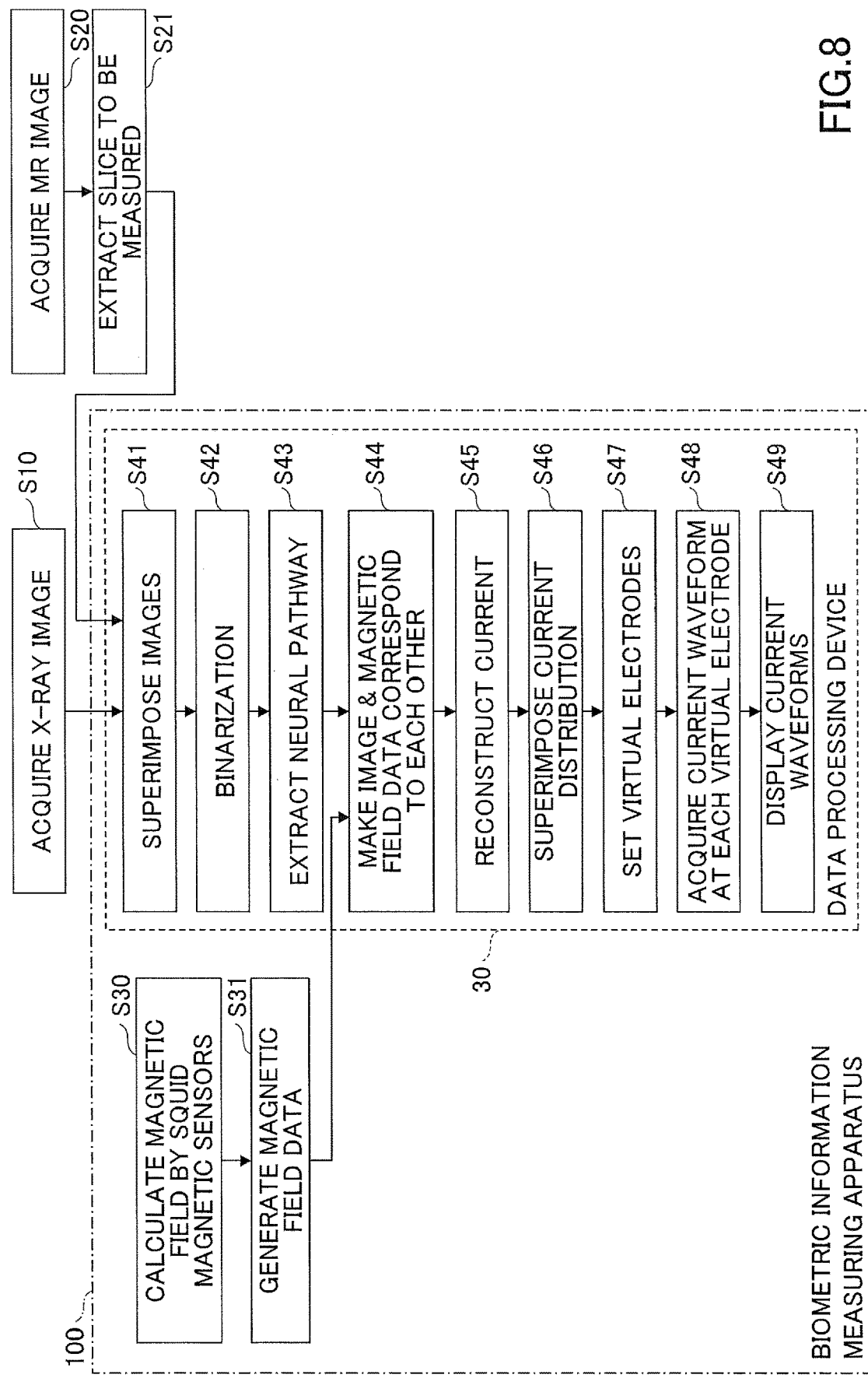
FIG. 8 is a flow diagram illustrating an example of a process of displaying current waveforms by the biometric information measuring apparatus illustrated in FIG. 1.

FIG. 8 is a flow diagram illustrating an example of a process of displaying the current waveforms by the biometric information measuring apparatus 100 illustrated in FIG. 1. In the example illustrated in FIG. 8, in order to acquire the morphological image of the parts of the subject to be measured, in step S10, the X-ray image of the subject is acquired using the X-ray machine, separately from measurement of the magnetic field signal of the subject. Further, in step S20, the MR image data of the subject is acquired using the magnetic resonance tomographic machine, and in step S21, a slice (MR image) to be measured is extracted from the MR image data. The process of step S21 may be performed by the data processing device 30. In step S20, the CT image may be used in place of the MR image.

By providing the X-ray machine inside the Shielded enclosure together with the SQUID magnetic sensors, it is possible to perform both radiography and measurement of the biometric magnetic field, in a state where the subject is lying on the bed inside the shielded enclosure. In this case, it is possible to accurately obtain the measuring positions of the magnetic field on the X-ray image, compared to the case where the X-ray image and the measurement of the biometric magnetic field are performed at different locations.

Among the processes from step S41 to step S49 performed by the data processing device 30, the processes of steps other than step S41 may be performed by the biometric information display method that is implemented based on the display program executed by the data processing device 30. The process of step S41 may also be performed by the display program executed by the data processing device 30.

In step S41, a process of generating a new morphological image, by superimposing the X-ray image and a sliced MR image, is performed using the data processing device 30. For example, the images may be superimposed by the operator of the data processing device 30, by moving and rotating one of the two images displayed on the display device 90 on the screen of the display device 90 using the input device 80, such as the mouse or the like. In this case, the input controller 40 accepts the operation performed by the operator, and the image display section 51 moves or rotates the image displayed on the display device 90 according to the accepted operation. The superimposed images are stored in the storage 70, as the morphological image data 72. In the following description, the operator of the data processing device 30 may also be simply referred to as the operator.

The process of superimposing the X-ray image and the MR image may be performed automatically using an image recognition technique. In this case, it is possible to utilize the machine learning technique, such as the deep learning or the like. In the case where the images are superimposed automatically, the process of step S41 may be performed by a superimposing processor (not illustrated) provided in the operation controller 60.

Next, in step S42, the data processing device 30 binarizes the MR image superimposed with the X-ray image, to generate a binary image, and stores the generated binary image in the storage 70, as the morphological image data 72.

Next, in step S43, the pathway generating section 61 of the data processing device 30 automatically extracts the neural pathway using the binary image. In the case where the neural pathway is extracted based on the operation performed by the operator, the process of step S42 to binarize the image may be omitted. In this case, the pathway generating section 61 extracts the neural pathway by generating a curve (including a straight line) based on coordinates of a plurality of specified positions designated by the operator on the image while viewing the morphological image displayed on the display device 90.

In the case where the neural pathway is extracted based on the operation performed by the operator, the pathway generating section 61 may generate a Bezier curve from the coordinates of the plurality of specified positions designated by the operator. By generating the Bezier curve, it is possible to easily and finely adjust (or control) the neural pathway while viewing the morphological image, and to easily generate a curve that indicates a neural pathway almost identical to the actual neural pathway. In the case where the neural pathway is extracted automatically, the pathway generating section 61 may utilize the machine learning technique, such as the deep learning or the like.

The image display section 51 displays the neural pathway extracted by the pathway generating section 61, by superimposing the neural pathway on the morphological image displayed on the screen of the display device 90. The pathway generating section 61 stores the coordinates of the extracted neural pathway on the image, the formula of the curve, or the like, in the storage 70. The binarization process of step S42 may also be omitted in the case where the neural pathway is extracted automatically, and in this case, the pathway generating section 61 automatically extracts the neural pathway using the image superimposed in step S41.

By using the MR image, it is possible to obtain detailed morphological information related to the manner in which the nerve of the subject runs. For this reason, by superimposing (aligning) the X-ray image and the MR image in step S41, the MR image can be utilized to easily determine the neural pathway matching the axon nerve. Accordingly, in step S48 and step S49 which will be described later, it is possible to acquire and display the current waveform at the exact position of the nerve of interest.

On the other hand, in step S30, the biometric information measuring apparatus 100 measures the biometric magnetic field of the subject by the SQUID magnetic sensors, for example, in synchronism with an electrical pulse stimulation applied to the peripheral nerve of the subject. In step S31, the signal acquiring section 20 generates the digital magnetic field data based on the voltage output from the SQUID magnetic sensors in correspondence with the measured magnetic field, and stores the generated magnetic field data in the storage 70, as the biometric magnetic field data 71. Step S30 and step S31 are repeated. By the processes performed up to this point, preparations for acquiring the current waveform at the parts of the subject to be measured are completed.

In step S44, the operation controller 60 of the data processing device 30 uses the position of the marker MK illustrated in FIG. 6 as a reference, for example, and coordinates the measuring position of the magnetic field data within the image in which the neural pathway is extracted, so as to correspond to the position of the marker MK. More particularly, the operation controller 60 detects the positions of the plurality of SQUID magnetic sensors within the image in which the neural pathway is extracted, from the magnetic field data of the marker MK measured by the SQUID magnetic sensors, and the marker MK appearing in the X-ray image. The correspondence between the image and the measuring positions of the magnetic field data, may be performed by the reconstruction analyzing section 63, or may be performed by a dedicated circuit or means (not illustrated).

Next, in step S45, the reconstruction analyzing section 63 reconstructs the current component, based on the magnetic field data at each measurement time or timing. In this case, the current component is reconstructed for each of the voxels illustrated in FIG. 5. The reconstruction analyzing section 63 stores the current information indicating the direction, intensity, coordinates, or the like of the current obtained by the reconstruction in the storage 70, as the morphological image data 72.

Next, in step S46, the reconstruction analyzing section 63 instructs the image display section 51 to display the arrows representing the direction and intensity of the current for each of the voxels obtained by the reconstruction, on the image superimposed in step S41. In addition, the reconstruction analyzing section 63 extracts the positions having the same current intensity in the image, based on the intensity of the current for each of the voxels, and displays the extracted positions in a state superimposed on the image, as the current intensity distribution. The reconstruction analyzing section 63 stores information indicating the current intensity distribution in the storage 70, as morphological image data 72. Hence, as illustrated in FIG. 7, for example, the X-ray image or the like, and the current distribution (arrows of the current and the current intensity distribution) reconstructed at each measurement time or timing, are superimposed and displayed on the screen.

Next, in step S47, the virtual electrode generating section 62 sets a predetermined number of virtual electrodes VEc, spaced apart from each other, on the neural pathway extracted in step S43. The number and the spacing of the virtual electrodes VEc may be preset by the operator, or the like. In addition, the virtual electrode generating section 62 sets the virtual electrodes VEl and VEr on both sides of each of the virtual electrodes VEc in the direction perpendicular to the neural pathway. The virtual electrode generating section 62 stores the coordinates of the set virtual electrodes VEc, VEl, and VEr on the image in the storage 70, as the morphological image data 72.

Figure 10:
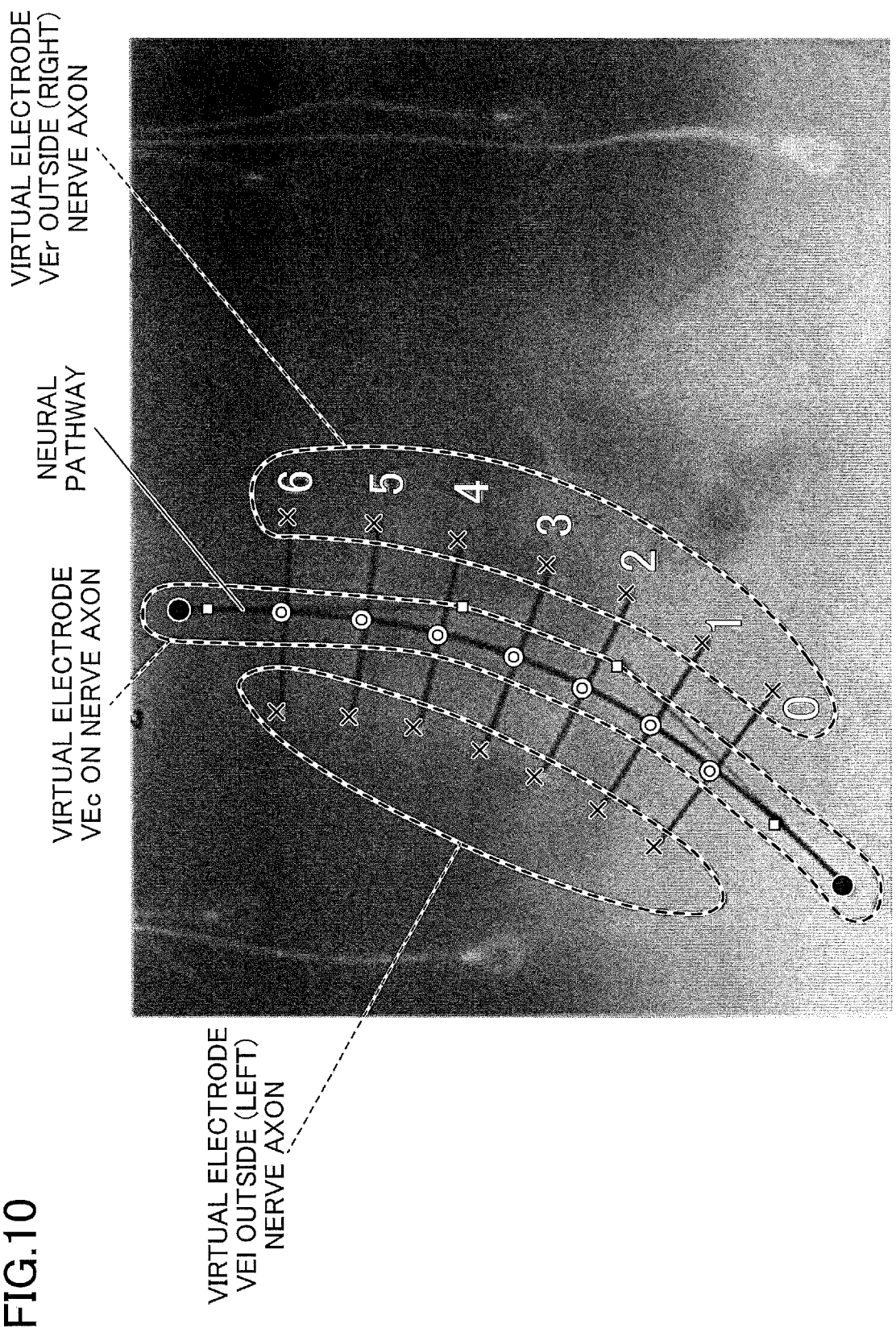
FIG. 10 is a diagram for explaining an example in which virtual electrodes are set along the neural pathway running from the right foot to the lumbar part.
Figure 15:
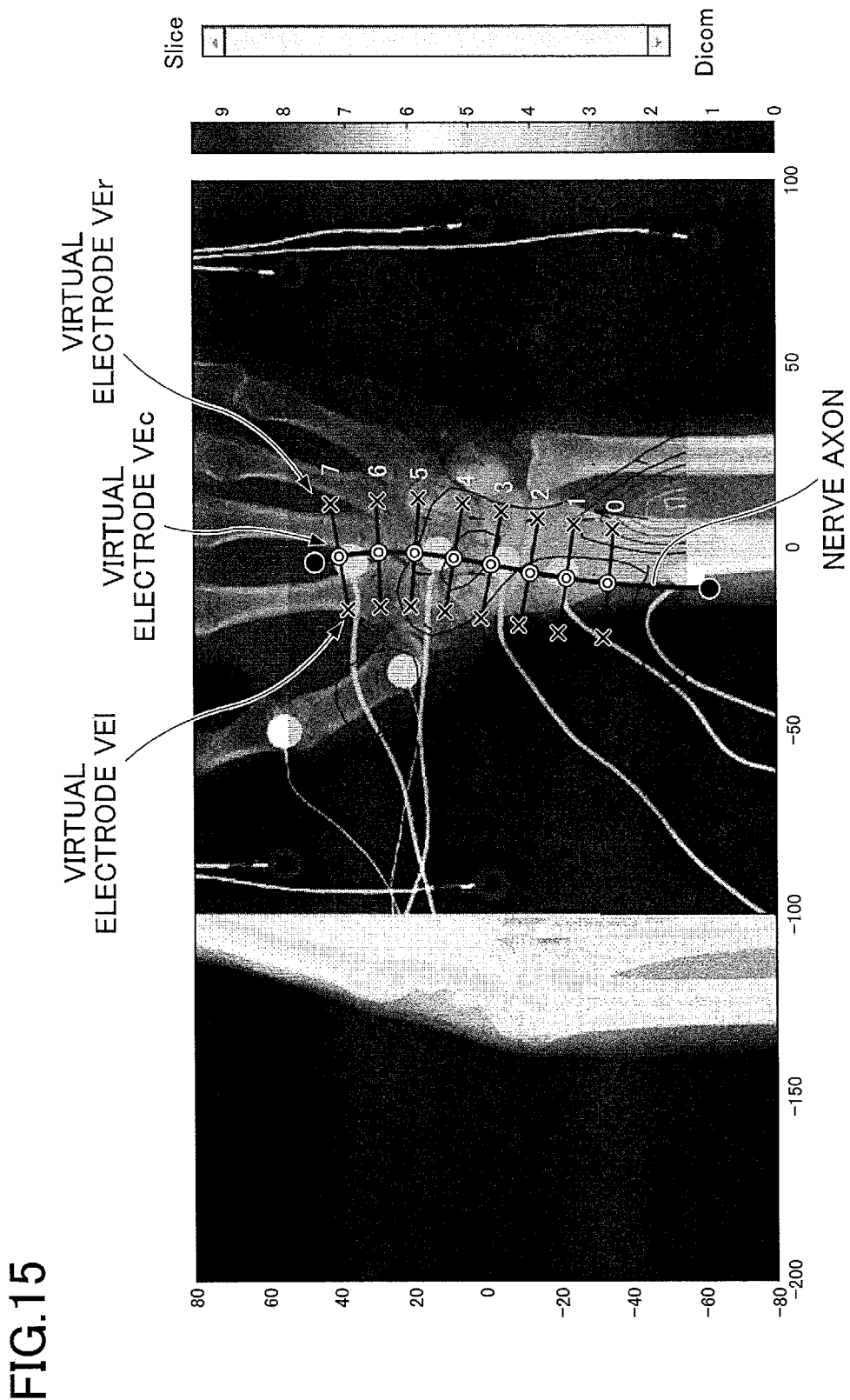
FIG. 15 is a diagram for explaining an example in which the virtual electrodes are set along the neural pathway of a carpal tunnel part.

The virtual electrode generating section 62 instructs the image display section 51 to superimpose and display the set virtual electrodes VEc and the set virtual electrodes VEl and VEr on the image displaying the neural pathway. Hence, as illustrated in FIG. 10, FIG. 15, and FIG. 17 which will be described later, the virtual electrodes VEc set on the neural pathway (nerve axon), and the virtual electrodes VEl, VEr, or the like set on both sides of each of the virtual electrodes VEc, are superimposed on the X-ray image or the like and displayed on the display device 90.

Next, in step S48, the current component extracting section 64 acquires the current data, varying with the lapse of time, at each of the virtual electrodes VEc, VEl, and VEr, as the current waveforms Then, in step S49, the current component extracting section 64 instructs the waveform display section 52 to display the acquired current waveforms on the screen of the display device 90.

Figure 11:
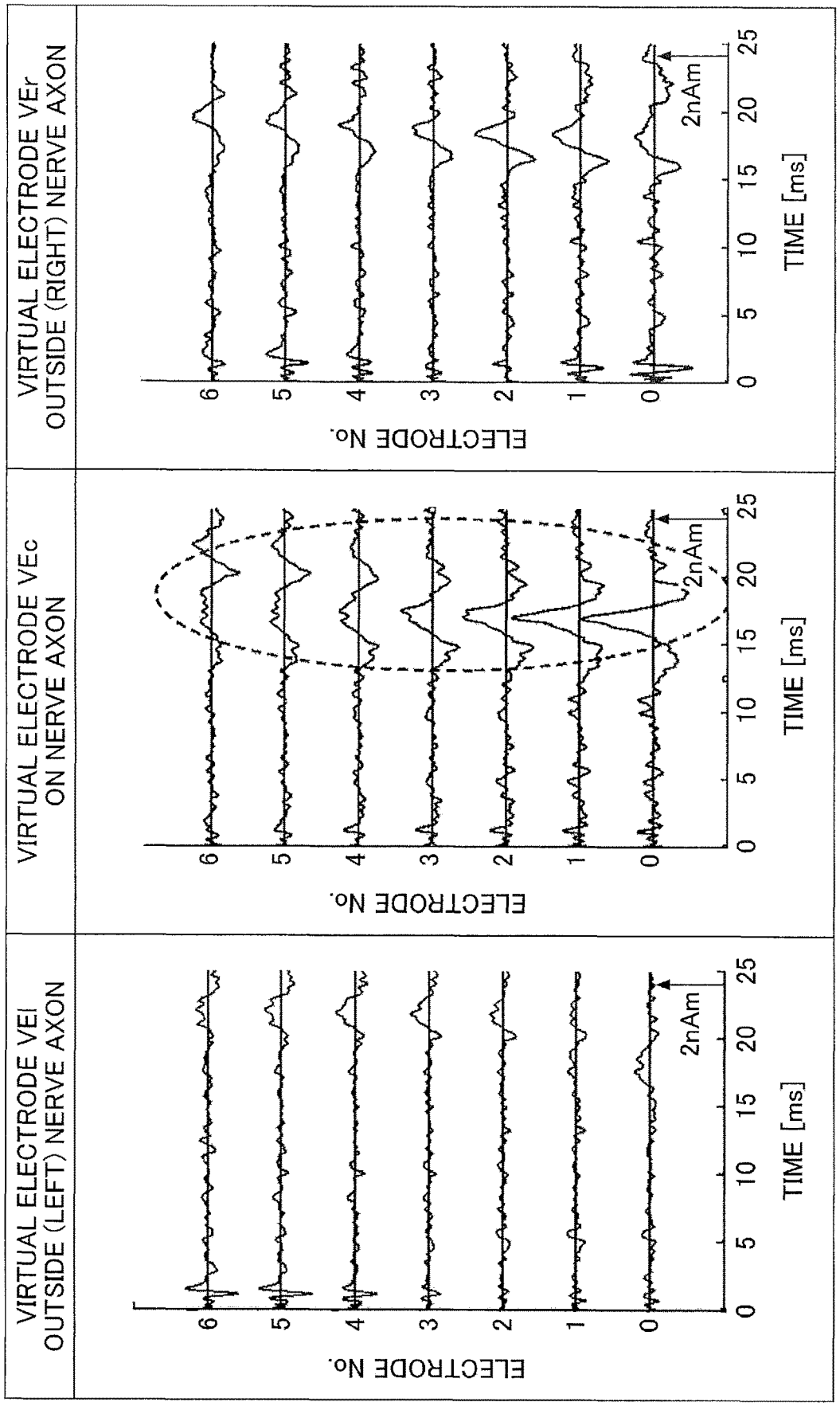
FIG. 11 is a diagram for explaining an example of the current waveforms at the virtual electrodes illustrated in FIG. 10.

The waveform display section 52 displays the time variation of the current component extracted by the current component extracting section 64 at each of the virtual electrodes VE, on the display device 90, as the current waveform. For example, the current waveform may be displayed in a window of the screen, separate from the window in which the morphological image is displayed on the screen of the display device 90. By displaying the current waveform at each of the virtual electrodes VE, it becomes possible to easily compare the current waveforms with potential measurement results obtained by the electromyograph or the like. By the processes performed up to this point, a series of processes for displaying the current waveforms is completed. An example of the display of the current waveforms is illustrated in FIG. 11.

Figure 9:
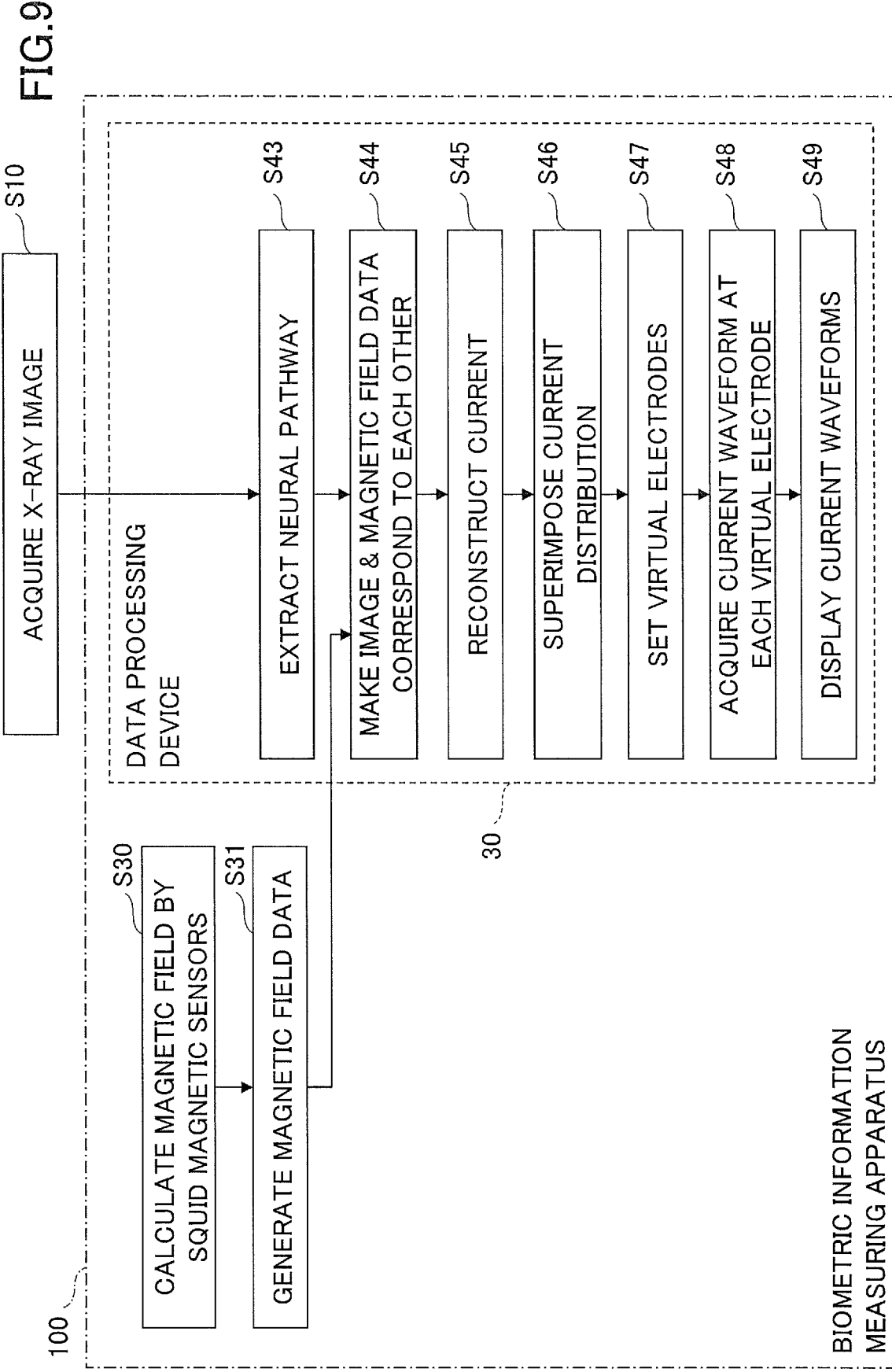
FIG. 9 is a flow diagram illustrating another example of the process of displaying the current waveforms by the biometric information measuring apparatus illustrated in FIG. 1.

FIG. 9 is a flow diagram illustrating another example of the process of displaying the current waveforms by the biometric information measuring apparatus 100 illustrated in FIG. 1. A detailed description of steps that are same as the steps illustrated in FIG. 8 will be omitted. The process illustrated in FIG. 9 is similar to the process illustrated in FIG. 8, except that in FIG. 9, the neural pathway is extracted using only the X-ray image, and no binarization of the image is performed. In other words, steps S20, S21, S41, and S42 in FIG. 8 are deleted in the process illustrated in FIG. 9.

In step S43, the pathway generating section 61 extracts the neural pathway using the X-ray image. The neural pathway may be extracted based on the coordinates of a plurality of specified positions on the image designated by the operator, or may be extracted automatically utilizing the machine learning technique, such as the deep learning or the like.

The neural pathway may be extracted using only the MR image. In this case, step S20 and step S21 illustrated in FIG. 8 are performed in place of step S10 illustrated in FIG. 9, and step S43 is performed thereafter. In the case where the neural pathway is extracted automatically using only the MR image, a process corresponding to step S42 that binarizes the MR image, may be additionally performed before step S43.

FIG. 10 is a diagram for explaining an example in which the virtual electrodes VE are set along the neural pathway running from the right foot to the lumbar part. FIG. 10 illustrates an image in which the neural pathway and the virtual electrodes VEc, VEl, and VEr are superimposed on the X-ray image, and displayed on the screen of the display device 90 within an image display window for displaying an image. In the image illustrated in FIG. 10, a lower left portion corresponds to the right foot, a lower right portion corresponds to a left foot, and an upper portion corresponds to the lumbar part. The image illustrated in FIG. 10 is displayed on the screen of the display device 90 by the processes of step S43 and step S47 illustrated in FIG. 8 and FIG. 9. As illustrated in FIG. 17, arrows representing the current component of each of the voxels, and a current intensity distribution, may be superimposed on the image illustrated in FIG. 10.

In the example illustrated in FIG. 10, a curved neural pathway, extracted in correspondence with the nerve axon running from the right foot to the lumbar part, is represented by a black bold solid line. The virtual electrode VEc set at a plurality of positions is displayed as a double circle, and the virtual electrodes VEl and VEr set at a plurality of positions are displayed as symbols X. The virtual electrodes VEc are set at a specified spacing designated by the operator, and are equally spaced in this example. For example, the neural pathway may be represented by the Bezier curve. Both ends of the extracted neural pathway are represented by black circles with white bordering. Four small white rectangles arranged along the neural pathway represent specified positions designated by the operator to draw the Bezier curve. The neural pathway may be drawn freehand by the operator.

Numbers displayed adjacent to the virtual electrodes VEr indicate electrode numbers that are assigned to identify each of the virtual electrodes VEc, and the virtual electrodes VEl and VEr corresponding to each of the virtual electrodes VEc. The virtual electrode VEc and each of the virtual electrodes VEl and VEr, assigned a common electrode number, are connected to each other by black bold solid lines. Since the actual screen may display the image in full color, various lines and marks may be displayed in different colors for easy identification.

As illustrated in FIG. 10, in this embodiment, the neural pathway can be set to the curved shape of the actual nerve axon, and the virtual electrodes VEc, VEl, and VEr can be set to arbitrary positions. For this reason, it is possible to extract the current waveform at an arbitrary position along the shape of the nerve axon, thereby enabling correct evaluation of the intra-axonal current and the volume current.

The shape of the neural pathway can be repeatedly varied, by accepting, by the position input section 41, an operation performed by the operator using the mouse or the like, to move the small white rectangles. In addition, the number of virtual electrodes VEc, VEl, and VEr, and the spacings of the virtual electrodes VEc, VEl, and VEr, can be freely set and reset, by accepting, by the position input section 41, an operation performed by the operator using the input device 80, such as the mouse, the keyboard, or the like.

The varied neural pathway and virtual electrodes VE are superimposed on the image, and displayed in a refreshed state. In other words, the position input section 41 accepts an instruction to vary the neural pathway and the virtual electrodes VE on the image, the pathway generating section 61 varies the shape of the neural pathway based on the instruction, and the image display section 51 superimposes and displays the varied neural pathway together with the moved virtual electrodes VE on the image in the refreshed state.

In a case where the shape of the neural pathway to be set is varied, or at least one of the number and the spacing of the virtual electrodes VE is varied, the current component extracting unit 64 reextracts the current component at the varied (or moved) virtual electrodes VE, and regenerates the current waveform based on the reextracted current component. The waveform display section 52 displays the regenerated current waveform on the screen of the display device 90 in the refreshed state. Hence, the shape of the neural pathway and the positions of the virtual electrodes VE may be reset repeatedly, until the current waveform, that enables the evaluation, diagnosis, examination, or the like, can be obtained.

In the case where the virtual electrodes VE are set by extracting the neural pathway using only the X-ray image, it becomes possible to perform both the radiography and the measurement of the biometric magnetic field of the subject inside the shielded enclosure as described above, thereby enabling the measuring positions of the magnetic field in the X-ray image to be accurately obtained.

FIG. 11 is a diagram for explaining an example of the current waveforms at the virtual electrodes VEc, VEl, and VEr illustrated in FIG. 10. The current waveforms (time variations of the current intensities) are displayed for each of the virtual electrodes VEc, VEl, and VEr using a common time base for all of the electrode numbers. The current waveforms illustrated in FIG. 11 are displayed in waveform display windows that are different from the image display window of the screen of the display device 90, by the processes of step S48 and step S49 illustrated in FIG. 8 and FIG. 9. Numerical values illustrated at the bottom right of each graph in FIG. 11 (in this example, 2 nAm) indicate current dipoles.

Variations in the current flowing through the nerve axon can be observed from the current waveform at the virtual electrode VEc, and variations in the volume current flowing into the nerve axon can be observed from the current waveforms at each of the virtual electrodes VEl and VEr. For example, current may be evaluated by the latency, which is the time from the application of the electrical stimulation to the peripheral nerve of the subject until the current value varies greatly, and this latency can be detected from a peak value of the current waveform.

In FIG. 11, in a region of the current waveform at the virtual electrode VEc encircled by an oval dotted line, the latency increases for the virtual electrode VEc having the larger electrode number, indicating that the electrical signal is transmitted from the side closer to the peripheral nerve to the side closer to the central nerve of the nerve axon. By setting the neural pathway according to the curved shape of the actual nerve axon, and detecting the current by setting the virtual electrodes VEc on the set neural pathway, the variation in the current flowing through the nerve axon can be determined from a single graph of the current waveform. The graph of the current waveform may be one of the graph of the current waveform at the virtual electrode VEc illustrated at a center portion of FIG. 11, the graph of the current waveform at the virtual electrode VEl illustrated at a left portion of FIG. 11, and the graph of the current waveform at the virtual electrode VEr illustrated at a right portion of FIG. 11.

In FIG. 11, the current waveform at the virtual electrode VEl is small compared to the current waveforms at the virtual electrode VEc and VEr. This is because, when the virtual electrodes VEl are set from the right foot toward the lumbar part as illustrated in FIG. 10, particularly the virtual electrode VEl on the side closer to the right foot is located at the end of the subject, thereby making the current component reconstructed from the magnetic field data small. However, by setting the virtual electrodes VEl and VEr on both sides of each of the virtual electrodes VEc, it is possible to increase the possibility of detecting the waveform of the volume current flowing into the nerve axon at either the virtual electrode VEl or the virtual electrode VEr.

Figure 12:
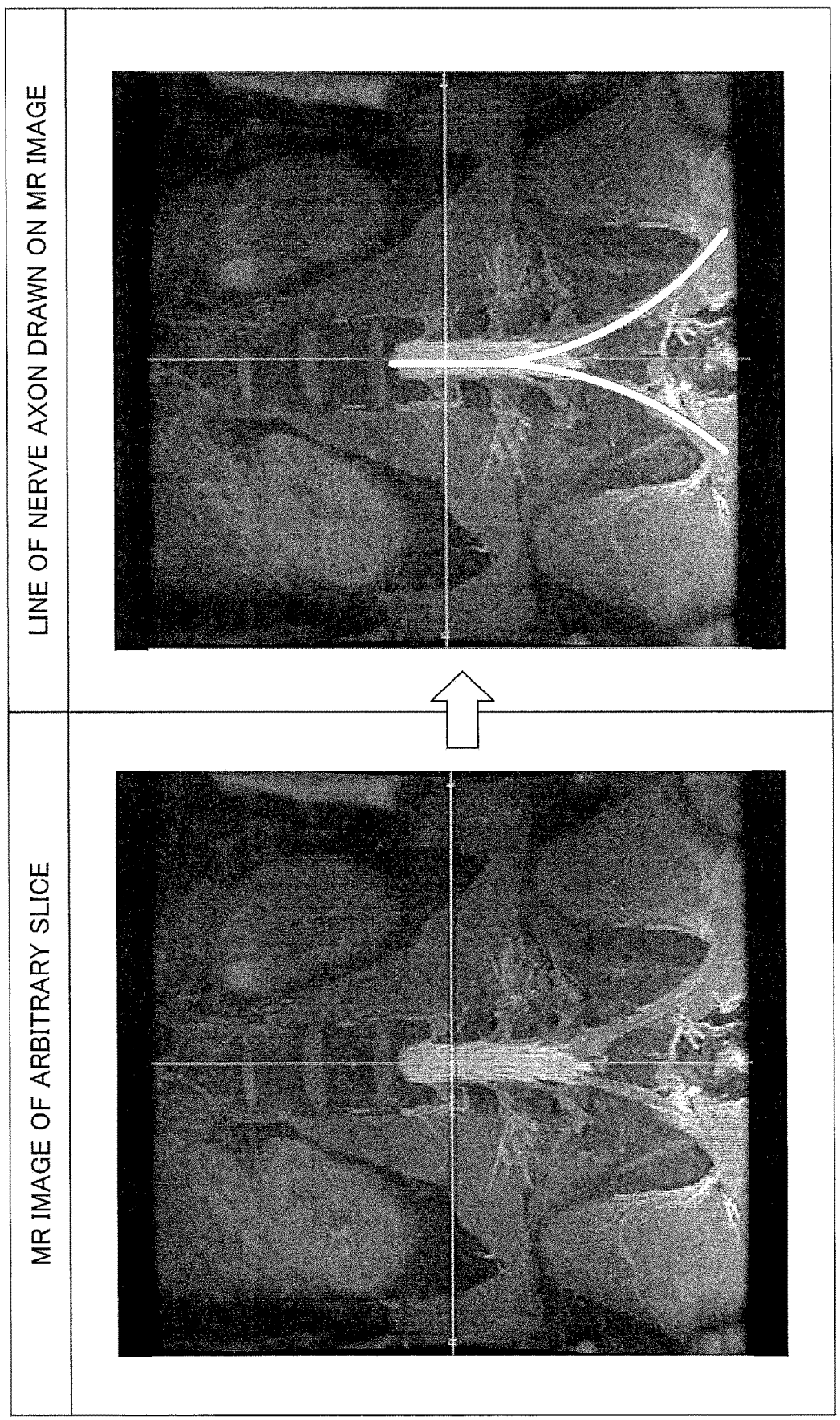
FIG. 12 is a diagram for explaining an example in which the neural pathway is extracted using an MR image.

FIG. 12 is a diagram for explaining an example in which the neural pathway is extracted using the MR image. When extracting the neural pathway using the MR image, step S20 and step S21 illustrated in FIG. 8 are performed instead of step S10 illustrated in FIG. 9, and step S43 is performed thereafter. A left portion of FIG. 12 illustrates the MR image before the neural pathway is extracted, and a right portion of FIG. 12 illustrates the MR image after the neural pathway is extracted.

In the example illustrated in FIG. 12, both the neural pathway running from the right foot to the lumbar part, and the neural pathway running from the left foot to the lumbar part, are extracted, as represented by thick white lines in the right portion of FIG. 12. However, it is possible to extract only one of these two neural pathways. In addition, the neural pathways may be extracted, based on the coordinates of the plurality of specified positions on the image designated by the operator, or may be extracted automatically utilizing the machine learning technique, such as the deep learning or the like.

By using the MR image, it is possible to obtain the detailed morphological information related to the manner in which the nerve of the subject runs. For this reason, after the neural pathway is extracted using the MR image, for example, it is possible to align the extracted neural pathway (that is, superimpose the image of the extracted neural pathway) to the X-ray image. Further, the binary image may be used when automatically extracting the neural pathway using the MR image.

Comparative Examples

Figure 13:
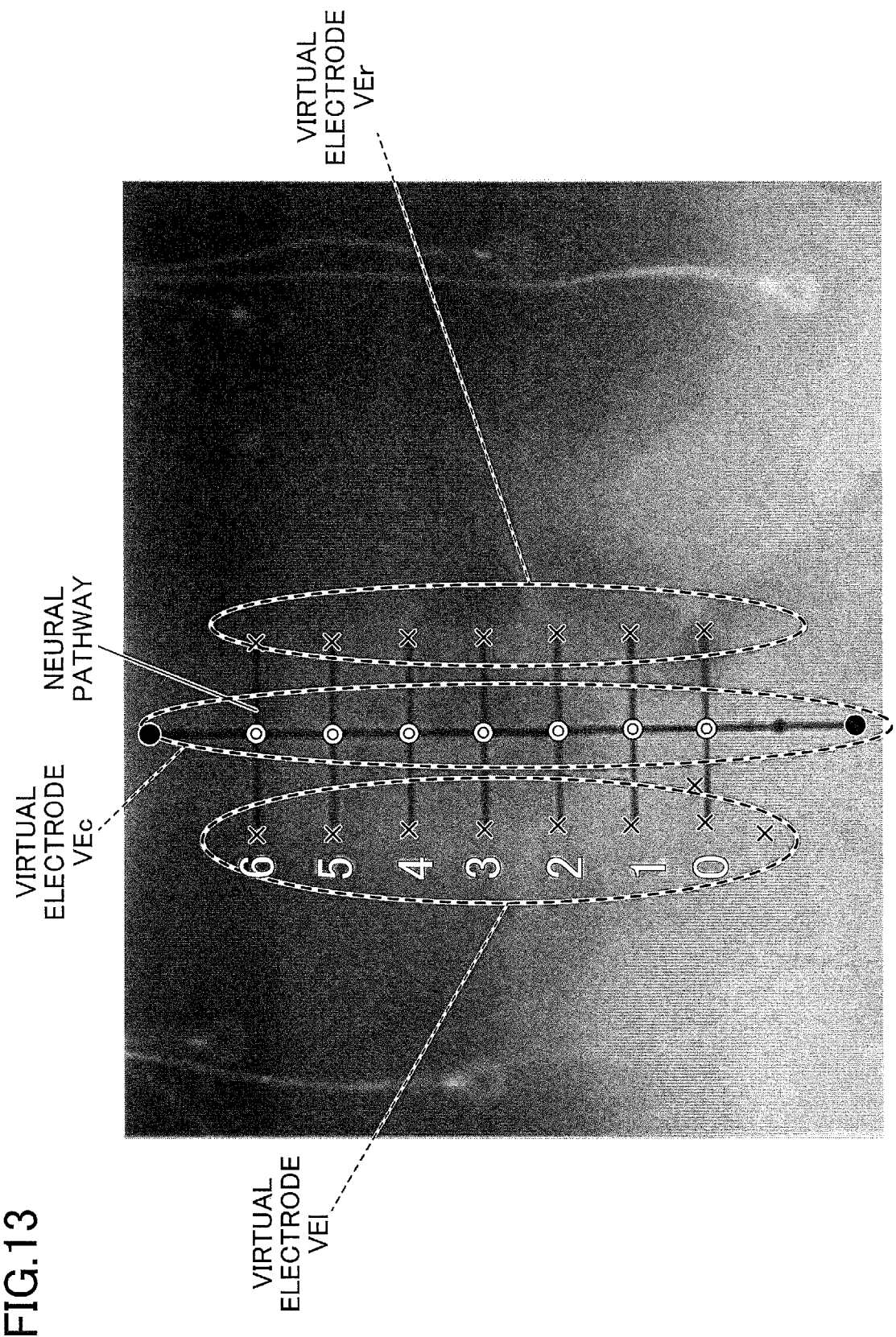
FIG. 13 is a diagram for explaining an example (comparative example) in which the neural pathway is set linearly.

FIG. 13 is a diagram for explaining an example (comparative example) in which the neural pathway is set linearly. In FIG. 13, a detailed description of the same elements as in FIG. 10 will be omitted. The X-ray image illustrated in FIG. 13 is similar to that of FIG. 10, and is a captured image, from the foot to the lumbar part of the subject.

The virtual electrodes VEc set on the neural pathway is not aligned with the nerve axon, because the neural pathway is not aligned to the nerve axon when the neural pathway is set linearly. In addition, the virtual electrodes VEl and VEr, which are set on both sides of each of the virtual electrodes VEc, do not extend along both sides of the nerve axon.

Figure 14:
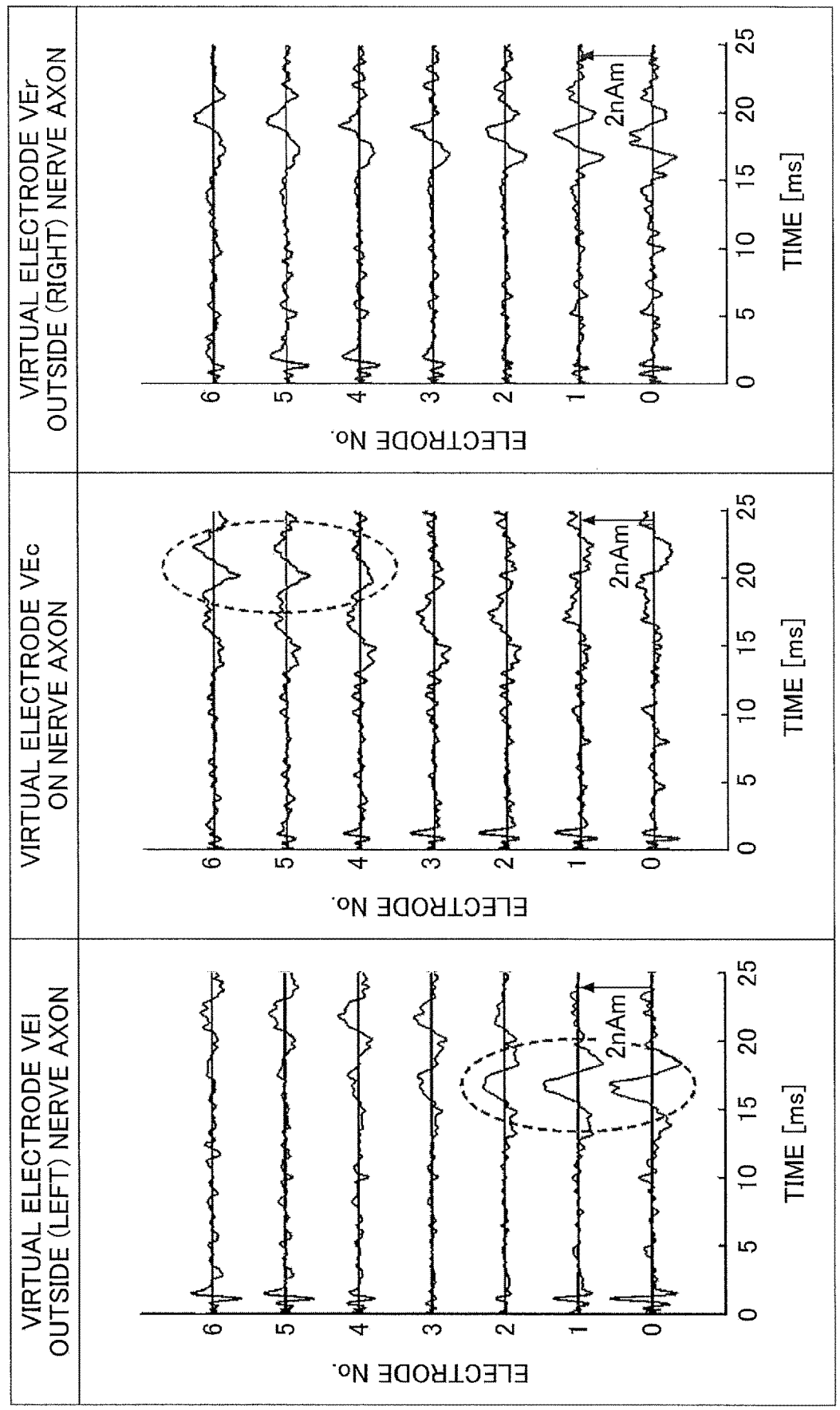
FIG. 14 is a diagram for explaining an example of the current waveforms at the virtual electrodes illustrated in FIG. 13.

FIG. 14 is a diagram for explaining an example of the current waveforms at the virtual electrodes VEc, VEl, and VEr illustrated in FIG. 13. In FIG. 14, a detailed description of the same elements as in FIG. 11 will be omitted. As illustrated in FIG. 6, the actual neural pathway is curved. For this reason, when the virtual electrodes VE are set linearly, the current waveform flowing through the actual nerve axon becomes separated into the current waveform at the virtual electrode VEl and the current waveform at the virtual electrode VEc. In FIG. 14, the current waveforms flowing through the nerve axon are separated and displayed separately as waveforms at the virtual electrodes VEl having the electrode numbers No. 0 through No. 2 surrounded by a dotted oval and a latency of approximately 16.5 ms, and waveforms at the virtual electrodes VEl having the electrode numbers No. 4 through No. 6 surrounded by a dotted oval and a latency of approximately 22 ms.

In this case, an evaluator, such as a physician or the like, who evaluates the nerve function of the subject, is required to evaluate the state of the current flowing through the nerve axon, by adding the current waveforms at the virtual electrodes VEl and the current waveforms at the virtual electrodes VEc in the head of the evaluator. In addition, the positions of the virtual electrodes VEc are deviated from the neural pathway of the actual nerve axon, and the virtual electrodes VEl and VEr are not parallel to the neural pathway of the actual nerve axon. For this reason, the MCV calculated using the latencies of the current waveforms at the virtual electrodes VEc, for example, does not become the MCV of the actual nerve axon.

On the other hand, by enabling the neural pathway to be set to the curve, as illustrated in FIG. 10, it becomes possible to set the neural pathway and the virtual electrodes VE along the actual nerve axon. For this reason, it is possible to accurately and easily calculate the MCV of the actual nerve axon, using only the latencies of the current waveforms at the virtual electrodes VEc. In addition, the evaluator, such as the physician or the like, can evaluate the manner in which the intra-axonal current and the volume current flow, by simply observing the current waveforms at the virtual electrodes VEc.

Similarly, it is possible to accurately and easily calculate the MCV, based on the variation of the volume current, using only the latencies of the current waveforms at the virtual electrodes VEl or the virtual electrodes VEr. In addition, the evaluator, such as the physician or the like, can evaluate the manner in which the volume current flows, by simply observing the current waveforms at the virtual electrodes VEl or the virtual electrodes VEr.

FIG. 15 is a diagram for explaining an example in which the virtual electrodes VE are set along the neural pathway of a carpal tunnel part. In FIG. 15, a detailed description of the same elements as in FIG. 10 will be omitted. FIG. 15 illustrates an example that uses the X-ray image to set the virtual electrodes VEc, VEl, and VEr, similar to FIG. 10. The X-ray image in a right portion of FIG. 15 illustrating the wrist and vicinities thereof captured from the front, and the X-ray image in a left portion of FIG. 15 illustrating the wrist and the vicinities thereof taken from the side, are displayed on the screen of the display device 90. The X-ray image in the left portion of FIG. 15 may or may not be displayed, as appropriate.

When evaluating the neural pathway of the carpal tunnel that is shorter in length than the neural pathway of the lumbar part illustrated in FIG. 10, for example, the spacing of the virtual electrodes VEc is set smaller than in FIG. 10. Hence, a suitable number of virtual electrodes VEc can be set according to the size of the part to be evaluated.

Figure 16:
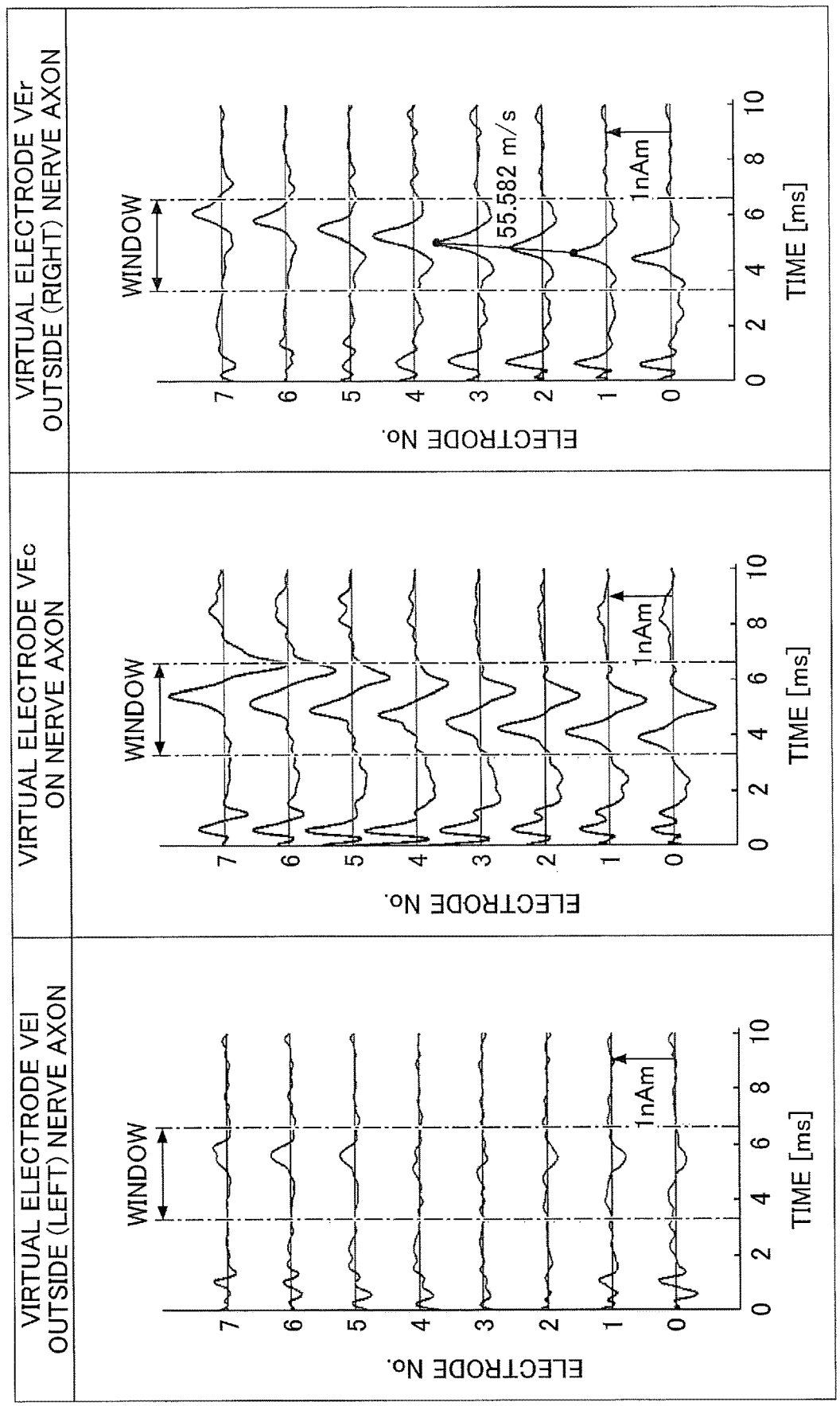
FIG. 16 is a diagram for explaining an example of the current waveforms at the virtual electrodes illustrated in FIG. 15.

FIG. 16 is a diagram for explaining an example of the current waveforms at the virtual electrodes VEc, VEl, and VEr illustrated in FIG. 15. In FIG. 16, a detailed description of the same elements as in FIG. 11 will be omitted. In the example illustrated in FIG. 16, a window for detecting the latency is set in the graphs of the current waveforms at the virtual electrodes VEc, VEl, and VEr. When setting this window, the operator may input a window set command, or select a window set command from a menu screen, for example, using the input device 80, such as the mouse, the keyboard, or the like. The waveform region designating section 42 instructs the waveform display section 52 to display straight lines indicating the window, based on the window setting command accepted from the input device 80. The waveform display section 52 displays two straight lines, indicated by one-dot chain lines in FIG. 16, and perpendicular to the time base, in a display region of each of the graphs, based on the instruction from the waveform region designating section 42.

Thereafter, the waveform region designating section 42 accepts an operation performed by the operator to select the one-dot chain line and move the selected one-dot chain line along the direction of the time base, and instructs the waveform display section 52 to move the display position of the one-dot chain line based on the accepted operation. As a result, it is possible to set the window that selects the range of a portion of the current waveform, that is, a time range of an arbitrary region sandwiched between the two one-dot chain lines. In other words, the position input section 41 receives an instruction that selects the range of the portion of the current waveform displayed on the display device 90, as positions of the two straight lines indicated by the one-dot chain lines in FIG. 16. The window may be displayed in the graph of each of the current waveforms illustrated in FIG. 11.

The latency of each of the current waveforms is detected within the window. For this reason, it is possible to prevent detection of an erroneous latency caused by a noise waveform or the like outside the window. In other words, the window is set to exclude current waveforms affected by noise caused by factors other than the body function or activity (that is, avoid the influence of magnetic fields from and vicinities of the biometric information measuring apparatus 100).

For example, the conduction velocity calculating section 65 detects peaks of the current waveform within the window, as feature points, and regards an appearing duration (time) of the peaks as the latency.

The waveform region designating section 42 accepts, from the operator via the input device 80, an instruction to select two current waveforms for calculating a conduction velocity CV of the nerve activity. In the example illustrated in FIG. 16, the waveform region designating section 42 accepts, from the operator, the positions of the current waveforms extracted at the virtual electrodes VEr having the electrode numbers No. 1 and No. 3, from among the plurality of current waveforms extracted at the virtual electrodes VEr, and an instruction to calculate the conduction velocity CV.

The conduction velocity calculating section 65 calculates the conduction velocity CV (55.582 m/s), based on the accepted instruction, and notifies the calculated conduction velocity CV to the waveform display section 52 together with information indicating the current waveforms used for the calculation of the conduction velocity CV. For example, the conduction velocity calculating section 65 calculates the conduction velocity CV, by dividing the distance between the two virtual electrodes VE from which the two current waveforms designated by the operator are extracted, by the latency difference between the latencies of the two current waveforms, as indicated by a formula illustrated in FIG. 3.

The waveform display section 52 displays the conduction velocity CV calculated by the conduction velocity calculating section 65, within the graph together with a line connecting the peaks of the current waveforms used for calculating the conduction velocity CV, for example. In other words, the waveform display section 52 displays the conduction velocity CV in correspondence with the current waveforms used for the calculating the conduction velocity CV. Accordingly, the evaluator, such as the physician or the like, can visually ascertain the conduction velocity CV, while viewing the displayed graph of the current waveforms. The example illustrated in FIG. 16 may be used for the diagnosis of whether the nerve in the carpal tunnel of the subject is pinched, compressed, or the like.

The distance between the two virtual electrodes VE is not a linear distance, and is the length along the neural pathway. In order to calculate the distance between the two virtual electrodes VE as the length of the neural pathway, the neural pathway extracted in step S43 illustrated in FIG. 8 is formed by a plurality of line segments. Accordingly, even in a case where the conduction velocity CV is calculated by a simple division, it is possible to accurately calculate the conduction velocity CV according to the length of the actual neural pathway.

Moreover, since the virtual electrodes VE are set at equal spacing, the conduction velocity calculating section 65 can calculate the conduction velocity CV from the current waveform data by a simple calculation. Furthermore, by setting the virtual electrodes VE at equal spacing, the evaluator, such as the physician or the like, can ascertain the approximate conduction velocity CV by simply viewing the graphs of the current waveforms, even before the conduction velocity CV is displayed.

The one-dot chain lines that are moved on the screen according to the instruction from the operator, may be the peak values (indicating latency) of the current waveforms at the two virtual electrodes VE. In this case, the position input section 41 accepts the input of the two electrode numbers used for calculating the conduction velocity CV, and the changes in the positions of the one-dot chain lines. Accordingly, the conduction velocity calculating section 65 can calculate the conduction velocity CV, by dividing the distance between the two virtual electrodes VE corresponding to the two electrode numbers that are input, by a time difference of the two one-dot chain lines.

Since the virtual electrodes VEl are set outside the region where the hand of the subject is located in the example illustrated in FIG. 15, the peak values that can detect the latency do not appear in the current waveforms at the virtual electrodes VEl illustrated in FIG. 16. Even in this case, it is possible to calculate the conduction velocity CV, using the current waveforms at the virtual electrodes VEr on the opposite side from the virtual electrodes VEl.

FIG. 17 is a diagram for explaining an example in which the virtual electrodes VE are set along the neural pathway running from the left foot to the lumbar part. In FIG. 17, a detailed description of the same elements as in FIG. 10 and FIG. 15 will be omitted. FIG. 17 illustrates an example that uses the X-ray image to set the virtual electrodes VEc, VEl, and VEr along the neural pathway running from the left foot to the lower back, similar to FIG. 10. Further, in FIG. 17, the arrows indicating the current components and the current intensity distribution are superimposed and displayed on the screen, together with the X-ray image, the neural pathway, and the virtual electrodes VE.

Figure 18:
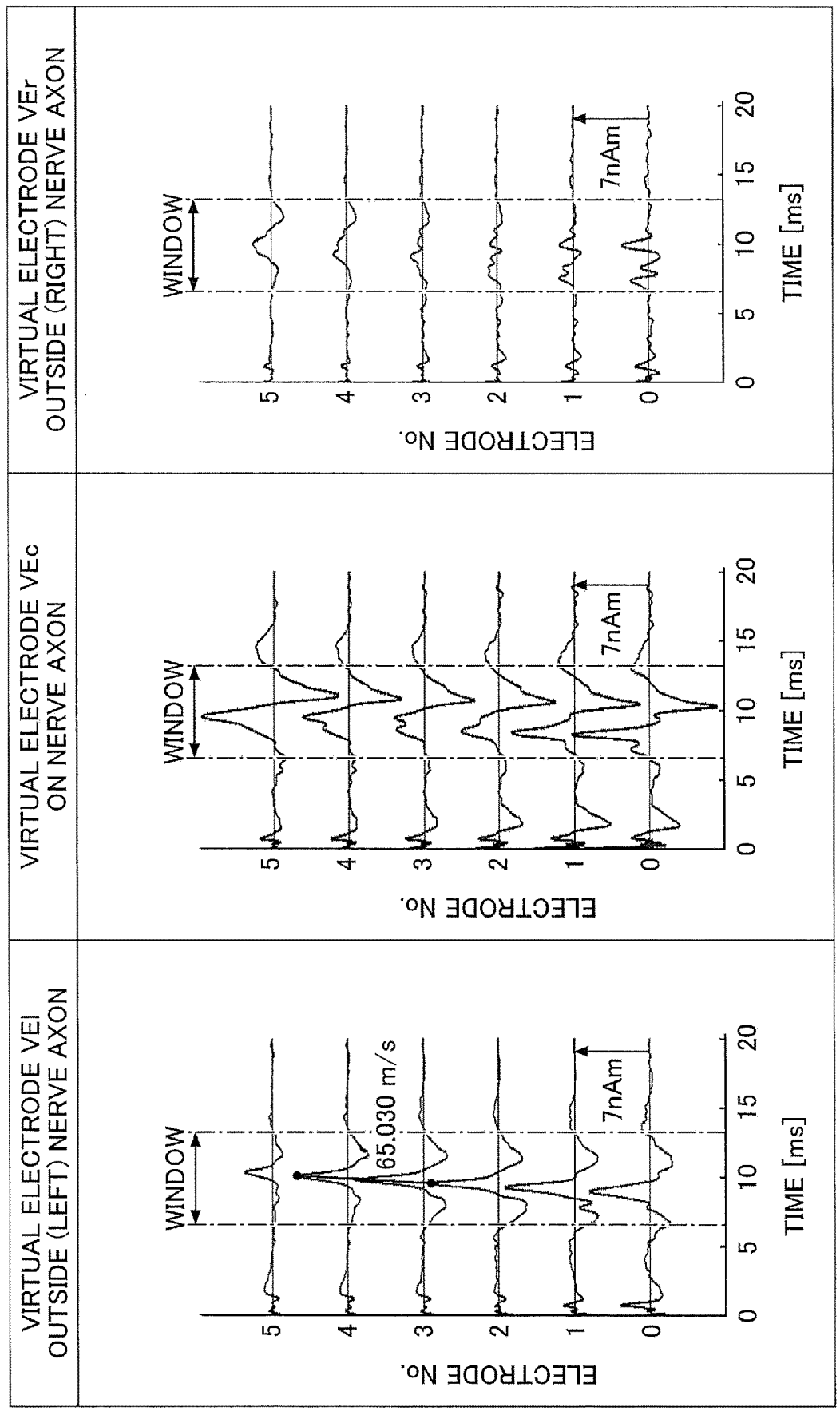
FIG. 18 is a diagram for explaining an example of the current waveforms at the virtual electrodes illustrated in FIG. 17.

FIG. 18 is a diagram for explaining an example of the current waveforms at the virtual electrodes VEc, VEl, and VEr illustrated in FIG. 17. In FIG. 18, a detailed description of the same elements as in FIG. 11 and FIG. 16 will be omitted. In the example illustrated in FIG. 18, the window for detecting the latency is set in the graphs of the current waveforms at the virtual electrodes VEc, VEl, and VEr, similar to FIG. 16.

In the example illustrated in FIG. 18, the waveform region designating section 42 accepts from the operator, the positions of the current waveforms extracted at the virtual electrodes VEl having the electrode numbers No. 2 and No. 4, from among the plurality of current waveforms extracted at the virtual electrode VEl, and the instruction to calculate the conduction velocity CV. The conduction velocity calculating section 65 calculates the conduction velocity CV (65.030 m/s), based on the accepted instruction.

The waveform display section 52 displays the conduction velocity CV calculated by the conduction velocity calculating section 65, in the graph, together with the line connecting the peaks of the current waveforms used for calculating the conduction velocity CV, for example. In the example illustrated in FIG. 18, it is possible to visualize the nerve activity of the lumbar part upon stimulation of the sciatic nerve, and the evaluator, such as the physician or the like, can utilize the visualized nerve activity for the diagnosis of the nerve activity or the like of a patient with disc herniation, for example.

Figure 19:
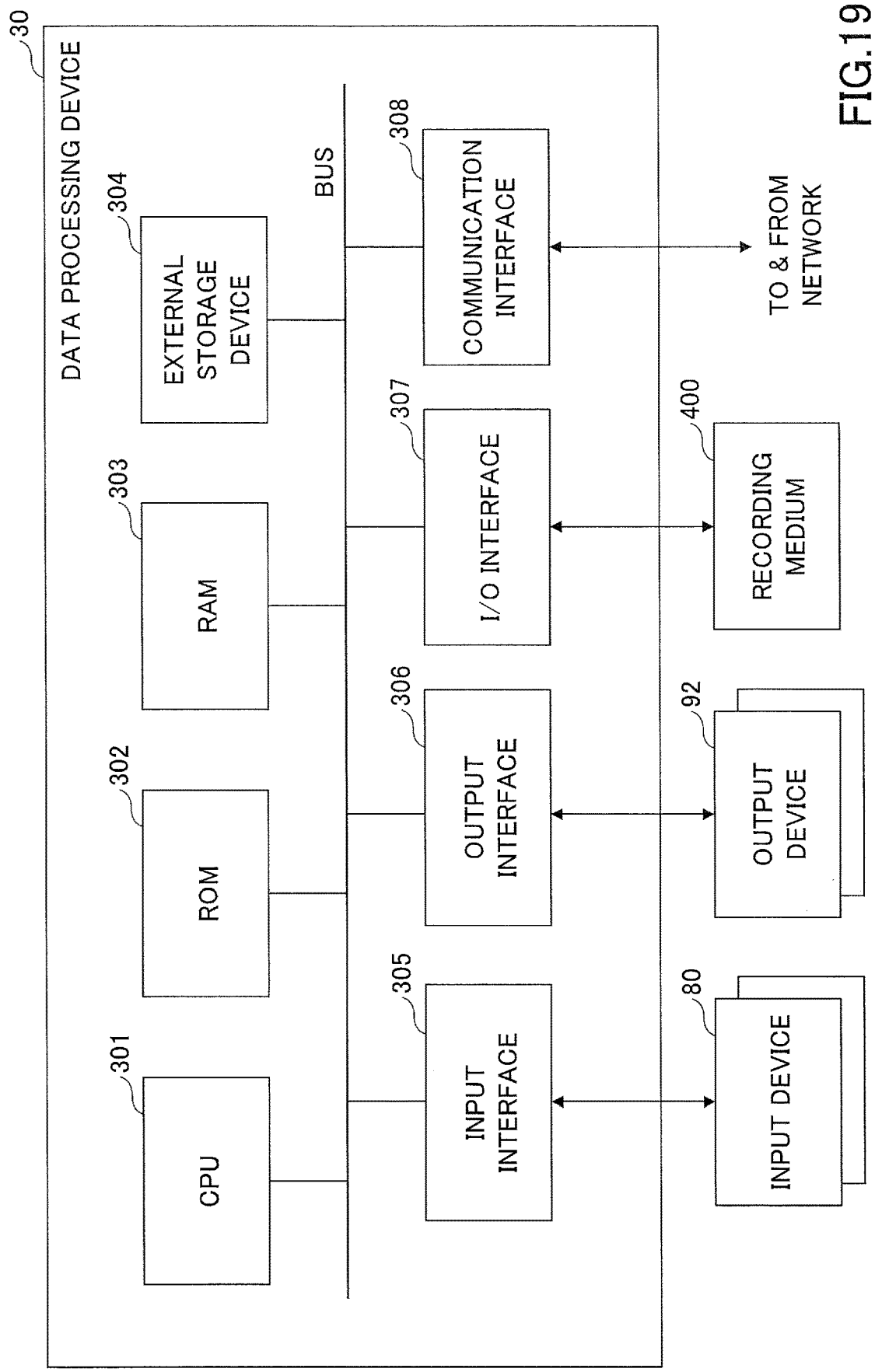
FIG. 19 is a block diagram illustrating an example of a hardware configuration of a data processing device illustrated in FIG. 1.

FIG. 19 is a block diagram illustrating an example of a hardware configuration of the data processing device 30 illustrated in FIG. 1. The data processing device 30 includes a CPU 301, a read only memory (ROM) 302, a random access memory (RAM) 303, and an external storage device 304. The data processing device 30 also includes an input interface 305, an output interface 306, an input-output (I/O) interface 307, and a communication interface 308. For example, the CPU 301, the ROM 302, the RAM 303, the external storage device 304, the input interface 305, the output interface 306, the I/O interface 307, and the communication interface 308 are connected to each other through a bus BUS.

The CPU 301 executes various programs, such as an operating system (OS), application programs, or the like, and controls the general operation of the data processing device 30. The ROM 302 stores basic programs, various parameters, or the like for enabling the various programs to be executed by the CPU 301. The RAM 303 stores the various programs executed by the CPU 301, data used by the various programs, or the like. The external storage device 304 may be formed by an HDD, a solid state drive (SSD), or the like, and stores the various programs loaded into the RAM 303. The various programs may include a display program for displaying the current waveforms, reconstructed from the magnetic field data, on display device 90.

The input device 80, such as the keyboard, the mouse, a tablet, or the like, which accepts the input from the operator or the like who operates the data processing device 30, is connected to the input interface 305. An output device 92, such as a display device (the display device 90 illustrated in FIG. 1, for example) that displays a screen (or display screen) or the like generated by the various programs executed by the CPU 301, a printer, or the like, is connected to the output interface 306.

A recording medium 400, such as a universal serial bus (USB) memory or the like, is connected to the I/O interface 307. For example, the recording medium 400 may store the various programs, such as the above described display program for displaying the current waveforms on the display device 90. In this case, the programs are transferred from the recording medium 400 to the RAM 303 through the I/O interface 307. The recording medium 400 may be formed by a compact disk-ROM (CD-ROM), a digital versatile disk (DVD, registered trademark), or the like. In this case, the I/O interface 307 includes an interface corresponding to the recording medium 400 connected thereto. The communication interface 308 connects the data processing device 30 to a network or the like.

The ROM 302, the recording medium 400, or the like are examples of a non-transitory computer-readable recording medium that stores one or more programs executed by a computer, such as the CPU 301.

Accordingly, in this embodiment, it is possible to generate the neural pathway from which the current components are to be extracted in the subject, by utilizing the morphological image of the subject. Hence, even in the case where the neural pathway is curved, it is possible to extract the current waveforms at arbitrary positions along the shape of the neural pathway, and enable correct evaluation of the intra-axonal current and the volume current. As a result, a detailed evaluation of the nerve function becomes possible, without imposing strain on the subject.

Since the plurality of virtual electrodes VEc can be set along the neural pathway, it becomes possible to evaluate the intra-axonal current, using only the current waveforms at the virtual electrodes VEc. In addition, since the plurality of virtual electrodes VEl and the plurality of virtual electrodes VEr can be set along both sides of the neural pathway, it becomes possible to evaluate the volume current flowing into the nerve axon, using only the current waveforms at the virtual electrodes VEl, or using only the current waveforms at the virtual electrodes VEr. Moreover, by setting the virtual electrodes VEl and VEr on both sides of each of the virtual electrodes VEc, it is possible to increase the possibility of detecting the waveform of the volume current from one of the virtual electrodes VEl and VEr, even when the waveform of the volume current cannot be detected from the other of the virtual electrodes VEl and VEr.

The shape of the neural pathway, and the number and the spacing of each of the virtual electrodes VEc, VEl, and VEr, may be reset repeatedly. Accordingly, the positions of the virtual electrodes VE may be varied repeatedly, until the current waveform that enables the evaluation, diagnosis, or the like is obtained. The pathway generating section 61 generates the Bezier curve as the curve representing the neural pathway, thereby enabling the operator to easily and finely adjust the neural pathway while viewing the morphological image, and thus, it is possible to easily generate the curve representing the neural pathway almost identical to the actual neural pathway.

By reconstructing (extracting) the current data from the magnetic field data, the conduction velocity CV can be calculated from the current waveform data without measuring the currents using the electromyograph or the like. In this case, by setting the time range of the current waveforms used for the calculation of the conduction velocity CV, it is possible to prevent the detection of the erroneous latency caused by the noise waveform or the like outside the window, and thus, it is possible to calculate the correct conduction velocity CV. For example, by setting the range in which the latency is to be detected, as the window sandwiched by the straight lines, it is possible to calculate the conduction velocity CV using a simple technique.

By superimposing the conduction velocity CV calculated by the conduction velocity calculating section 65 on the current waveforms, and displaying the superimposed image on the screen of the display device 90, it becomes possible for the evaluator, such as the physician or the like, to visually ascertain the conduction velocity CV while viewing the displayed graph of the current waveforms.

By setting the virtual electrodes VE at equal spacing, the conduction velocity calculating section 65 can calculate the conduction velocity CV from the current waveform data by a simple calculation. In addition, the evaluator, such as the physician or the like, can visually ascertain the approximate conduction velocity CV by simply viewing the graph of the current waveforms, even before the conduction velocity CV is displayed.

For example, by using the MR image that illustrates in detail the manner in which the nerve of the subject runs, it is possible to easily extract the neural pathway matching the axonal nerve, and to acquire and display the current waveform at the accurate position of the nerve of interest. By superimposing the X-ray image with the MR image, it is possible to ascertain the part to be measured that is displayed in the image, with reference to a skeletal system, for example.

According to each of the embodiments described above, it is possible to generate the neural pathway from which the current component is to be extracted in the subject, using the morphological image of the subject.

Each of the embodiments describes the example in which the current is reconstructed from the biometric magnetic field data of the subject, and the current waveforms at the virtual electrodes set along the neural pathway are displayed on the screen. However, the biometric magnetic field data of the subject may be used to measure the amount of magnetic field per magnetic sensor (per channel), and virtual measuring points for measuring the magnetic field may be set along the neural pathway, to display, on the screen, the magnetic field waveform at each of the virtual measuring points for measuring the magnetic field. In other words, the component of the waveforms displayed on the screen may be other than the current, provided that the component is a signal that can be expressed as a vector quantity.

Although the present disclosure is described heretofore based on the embodiments, the present disclosure is not limited to the described embodiments, and various variations, modifications, and substitutions may be made without departing from the scope of the present disclosure.

What is claimed is:

1. A biometric information display device comprising:
   a display controller configured to display a morphological image indicative of a morphology of a subject, on a display;
   an input controller configured to receive a designation of a specified position on the morphological image, and to receive a number of first virtual electrodes and a distance between two adjacent first virtual electrodes; and
   an operation controller configured to perform a process including
     generating a neural pathway based on the specified position on the morphological image,
     generating a plurality of first virtual electrodes on the neural pathway, and a second virtual electrode and a third virtual electrode on both sides of the neural pathway at each first virtual electrode of the plurality of the first virtual electrodes, based on the number of first virtual electrodes and the distance between the two adjacent first virtual electrodes, to generate a plurality of second virtual electrodes and a plurality of third virtual electrodes, and
     extracting current components at each first virtual electrode of the plurality of first virtual electrodes, each second virtual electrode of the plurality of second virtual electrodes, and at each third virtual electrode of the plurality of third virtual electrodes, based on current information reconstructed based on magnetic field measurement data generated by the subject,
   wherein the display controller displays current waveforms representing a time variation of the respective current components of the plurality of first virtual electrodes, the plurality of second virtual electrodes, and the plurality of third virtual electrode, on the display,
   wherein the input controller further receives
     a designation of a specified time range of one of the current waveforms of the plurality of first virtual electrodes, the plurality of second virtual electrodes, and the plurality of third virtual electrodes displayed on the display, and
     a designation of two specified current waveforms among the current waveforms of the plurality of first virtual electrodes, the plurality of second virtual electrodes, and the plurality of third virtual electrodes displayed on the display, and
   the operation controller performs the process further including
     calculating a conduction velocity of a stimulus within the subject, based on a time variation of a feature point of the one of the current waveforms within the specified time range, and calculating the conduction velocity between two virtual electrodes corresponding to the two specified current waveforms, based on a difference between appearance times of feature points of the two specified current waveforms, and the neural pathway between the two virtual electrodes.

2. The biometric information display device as claimed in claim 1, wherein
  the generating the neural pathway resets positions of the plurality of first virtual electrodes, the plurality of second virtual electrodes, and the plurality of third virtual electrodes, based on a change in at least one of the number of the plurality of first virtual electrodes and the distance between the two adjacent first virtual electrodes, and
  the extracting reextracts the current components of the plurality of first virtual electrodes, the plurality of second virtual electrodes, and the plurality of third virtual electrodes at the reset positions.

3. The biometric information display device as claimed in claim 1, wherein
  the display controller displays the current waveforms of the plurality of first virtual electrodes, the plurality of second virtual electrodes, and the plurality of third virtual electrodes on the display using a common time base,
  the input controller receives positions of two straight lines perpendicular to the common time base displayed in a display region of the current waveforms on the display, and
  the specified time range is a range sandwiched between the two straight lines received by the input controller.

4. The biometric information display device as claimed in claim 1, wherein
  the display controller displays the conduction velocity calculated by the calculating on the display in correspondence with the current waveforms used to calculate the conduction velocity.

5. The biometric information display device as claimed in claim 1, wherein the morphological image is one of an X-ray image, a computed tomography image, and a magnetic resonance image.

6. The biometric information display device as claimed in claim 1, wherein the generating the neural pathway generates the neural pathway using a Bezier curve according to a plurality of specified positions designated on the morphological image.

7. A biometric information display method to be implemented in a biometric information display device that includes a display controller configured to display a morphological image indicative of the morphology of a subject, and an input controller configured to receive a designation of a specified position on the morphological image, and to receive a number of first virtual electrodes and a distance between two adjacent first virtual electrodes, the biometric information display method comprising:
  generating a neural pathway based on the specified position on the morphological image;
  generating a plurality of first virtual electrodes on the neural pathway, and a second virtual electrode and a third virtual electrode on both sides of the neural pathway at each first virtual electrode of the plurality of the first virtual electrodes, based on the number of first virtual electrodes and the distance between the two adjacent first virtual electrodes, to generate a plurality of second virtual electrodes and a plurality of third virtual electrodes;
  extracting current components at each first virtual electrode of the plurality of first virtual electrodes, each second virtual electrode of the plurality of second virtual electrodes, and at each third virtual electrode of the plurality of third virtual electrodes, based on current information reconstructed based on magnetic field measurement data generated by the subject;
  displaying current waveforms representing a time variation of the respective current components of the plurality of first virtual electrodes, the plurality of second virtual electrodes, and the plurality of third virtual electrode, on a display
  receiving a designation of a specified time range of one of the current waveforms of the plurality of first virtual electrodes, the plurality of second virtual electrodes, and the plurality of third virtual electrodes displayed on the display;
  receiving a designation of two specified current waveforms among the current waveforms of the plurality of first virtual electrodes, the plurality of second virtual electrodes, and the plurality of third virtual electrodes displayed on the display; and
  calculating a conduction velocity of a stimulus within the subject, based on a time variation of a feature point of the one of the current waveforms within the specified time range, and calculating the conduction velocity between two virtual electrodes corresponding to the two specified current waveforms, based on a difference between appearance times of feature points of the two specified current waveforms, and the neural pathway between the two virtual electrodes.

8. The biometric information display method as claimed in claim 7, wherein the morphological image is one of an X-ray image, a computed tomography image, and a magnetic resonance image.

9. The biometric information display method as claimed in claim 7, wherein the generating the neural pathway generates the neural pathway using a Bezier curve according to a plurality of specified positions designated on the morphological image.

10. The biometric information display method as claimed in claim 7, wherein
  the generating the neural pathway resets positions of the plurality of first virtual electrodes, the plurality of second virtual electrodes, and the plurality of third virtual electrodes, based on a change in at least one of the number of the plurality of first virtual electrodes and the distance between the two adjacent first virtual electrodes, and
  the extracting reextracts the current components of the plurality of first virtual electrodes, the plurality of second virtual electrodes, and the plurality of third virtual electrodes at the reset positions.

11. A non-transitory computer-readable recording medium having stored therein a display program which, when executed by a computer of a biometric information display device that includes a display controller configured to display a morphological image indicative of the morphology of a subject, and an input controller configured to receive a designation of a specified position on the morphological image, and to receive a number of first virtual electrodes and a distance between two adjacent first virtual electrodes, causes the computer to perform a process comprising:
  generating a neural pathway based on the specified position on the morphological image;
  generating a plurality of first virtual electrodes on the neural pathway, and a second virtual electrode and a third virtual electrode on both sides of the neural pathway at each first virtual electrode of the plurality of the first virtual electrodes, based on the number of first virtual electrodes and the distance between the two adjacent first virtual electrodes, to generate a plurality of second virtual electrodes and a plurality of third virtual electrodes;

extracting current components at each first virtual electrode of the plurality of first virtual electrodes, each second virtual electrode of the plurality of second virtual electrodes, and at each third virtual electrode of the plurality of third virtual electrodes, based on current information reconstructed based on magnetic field measurement data generated by the subject;

displaying current waveforms representing a time variation of the respective current components of the plurality of first virtual electrodes, the plurality of second virtual electrodes, and the plurality of third virtual electrode, on a display receiving a designation of a specified time range of one of the current waveforms of the plurality of first virtual electrodes, the plurality of second virtual electrodes, and the plurality of third virtual electrodes displayed on the display;

receiving a designation of two specified current waveforms among the current waveforms of the plurality of first virtual electrodes, the plurality of second virtual electrodes, and the plurality of third virtual electrodes displayed on the display; and calculating a conduction velocity of a stimulus within the subject, based on a time variation of a feature point of the one of the current waveforms within the specified time range, and calculating the conduction velocity between two virtual electrodes corresponding to the two specified current waveforms, based on a difference between appearance times of feature points of the two specified current waveforms, and the neural pathway between the two virtual electrodes.

12. The non-transitory computer-readable recording medium as claimed in claim 11, wherein the morphological image is one of an X-ray image, a computed tomography image, and a magnetic resonance image.

13. The non-transitory computer-readable recording medium as claimed in claim 11, wherein the generating the neural pathway generates the neural pathway using a Bezier curve according to a plurality of specified positions designated on the morphological image.

14. The non-transitory computer-readable recording medium as claimed in claim 11, wherein
the generating the neural pathway resets positions of the plurality of first virtual electrodes, the plurality of second virtual electrodes, and the plurality of third virtual electrodes, based on a change in at least one of the number of the plurality of first virtual electrodes and the distance between the two adjacent first virtual electrodes, and
the extracting reextracts the current components of the plurality of first virtual electrodes, the plurality of second virtual electrodes, and the plurality of third virtual electrodes at the reset positions.

* * * * *